US010634684B2

(12) United States Patent
Yoshida et al.

(10) Patent No.: US 10,634,684 B2
(45) Date of Patent: Apr. 28, 2020

(54) METHOD FOR IDENTIFYING POLYUBIQUITINATED SUBSTRATE

(71) Applicant: Tokyo Metropolitan Institute of Medical Science, Tokyo (JP)

(72) Inventors: Yukiko Yoshida, Tokyo (JP); Yasushi Saeki, Tokyo (JP); Hikaru Tsuchiya, Tokyo (JP); Arisa Murakami, Tokyo (JP); Keiji Tanaka, Tokyo (JP)

(73) Assignee: TOKYO METROPOLITAN INSTITUTE OF MEDICAL SCIENCE, Tokyo (JP)

( * ) Notice: Subject to any disclaimer, the term of this patent is extended or adjusted under 35 U.S.C. 154(b) by 514 days.

(21) Appl. No.: 15/035,357

(22) PCT Filed: Nov. 13, 2014

(86) PCT No.: PCT/JP2014/080053
§ 371 (c)(1),
(2) Date: Jun. 4, 2018

(87) PCT Pub. No.: WO2015/072507
PCT Pub. Date: May 21, 2015

(65) Prior Publication Data
US 2018/0267052 A1    Sep. 20, 2018

(30) Foreign Application Priority Data

Nov. 15, 2013 (JP) ................................ 2013-237362

(51) Int. Cl.
*G01N 33/68* (2006.01)
*C12Q 1/527* (2006.01)
*C12Q 1/25* (2006.01)

(52) U.S. Cl.
CPC .......... *G01N 33/6842* (2013.01); *C12Q 1/25* (2013.01); *C12Q 1/527* (2013.01); *G01N 33/6818* (2013.01); *G01N 33/6848* (2013.01); *G01N 2440/36* (2013.01)

(58) Field of Classification Search
None
See application file for complete search history.

(56) References Cited

FOREIGN PATENT DOCUMENTS

WO    WO-03102172 A1 * 12/2003 ............. C07K 14/00

OTHER PUBLICATIONS

Melvin et al. Cell Biochem Biophys 2013 67:75-89 (Year: 2013).*
Peng (BMB Reports 2008 41: 177-183).*
Komander, et al. The Ubiquitin Code. Annual Review of Biochemistry (2012): 203-229; v-vii.
Grabbe, et al. The spatial and temporal organization of ubiquitin networks. Nat Rev Mol Cell Biol. 12:5 (May 2011): 295-307.
Hjerpe, et al. Efficient protection and isolation of ubiquitylated proteins using tandem ubiquitin-binding entities. EMBO Reports 10:11 (2009): 1250-1258.
Kim, et al. Systematic and Quantitative Assessment of the Ubiquitin-Modified Proteome. Molecular Cell Resource 44 (Oct. 21, 2011): 325-340.
Frescas, et al. Deregulated proteolysis by the F-box proteins SKP2 and Beta-TrCP: tipping the scales of cancer. Nat Rev Cancer 8:6 (Jun. 2008): 438-440.
Komander and Rape, Annual review of biochemistry, 2012, vol. 81, p. 203-229.
Grabbe, et al., Nature reviews. Molecular cell biology, 2011, vol. 12, p. 295-307.
Hjerpe, et al., EMBO reports, 2009, vol. 10, p. 1250-1258.
Kim, et al., Molecular Cell, 2011, vol. 44, p. 325-340.
Frescas and Pagano, Nature Reviews Cancer, 2008, vol. 8, p. 438-449.
Lopitz-Otsoa, F. et al., Integrative analysis of the ubiquitin proteome isolated using Tandem Ubiquitin Binding Entities (TUBEs), J.Proteomics, 2012, vol. 75, pp. 2998-3014.
Shi, Y. et al., A Data Set of Human Endogenous Protein Ubiquitination Sites, Molecular & Cellular Proteomics, 2011, vol. 10, No. 5, doi:10.1074/mcp.M110.002089.
International Search Report, PCT/JP2014/080053 dated Feb. 10, 2015, translation attached.

* cited by examiner

*Primary Examiner* — Changhwa J Cheu
(74) *Attorney, Agent, or Firm* — Thomas | Horstemeyer, LLP

(57) ABSTRACT

An object of the present invention is to provide a method for efficiently identifying a polyubiquitinated substrate which is generally not easily identified. The method for identifying a polyubiquitinated substrate includes (1) a step of expressing a trypsin-resistant polyubiquitin chain-binding protein and a ubiquitin ligase in a cell, (2) a step of isolating a complex that contains the trypsin-resistant polyubiquitin chain-binding protein from the cell having undergone the step (1), (3) a step of subjecting the complex isolated by the step (2) to trypsin digestion, and (4) a step of identifying a peptide that has a ubiquitination site from a digested material obtained by the step (3).

8 Claims, 9 Drawing Sheets

Specification includes a Sequence Listing.

1. COEXPRESSING UBIQUITIN LIGASE AND TRYPSIN-RESISTANT POLYUBIQUITIN CHAIN PROBE IN A CELL

2. ISOLATION OF UBUIQITINATED SUBSTRATE BY IMMUNOPRECIPITATION CAUSED BY ANTI-Flag ANTIBODY

3. TRYPSIN DIGESTION

4. PURIFICATION OF UBIQUITINATED PEPTIDE BY USING ANTI-diGLY ANTIBODY

5. IDENTIFICATION OF UBIQUITINATED SUBSTRATE AND UBIQUITINATION SITE BY USING LC-MS

FIG. 2

☐ Flag TAG
☐ MUTATED UBA DOMAIN

```
         10        20        30        40        50        60
ATGGACTACAAGGACGACGATGACAAGGGGATCATCAGATCTGGAGGTGGAGTAAATCCT
METAspTyrLysAspAspAspAspLysGlyIleIleArgSerGlyGlyGlyValAsnPro 70        80        90       100       110       120
CAGCTACAGAATCCAGAAGTCGCGTTTCAGCAACAACTGGAACAACTCAGTGCAATGGGA
GlnLeuGlnAsnProGluValAlaPheGlnGlnGlnLeuGluGlnLeuSerAlaMETGly 130       140       150       160       170       180
TTTTTGAACGCGGAAGCAAACTTGCAAGCTCTAATAGCAACAGGAGGTGATATTAATGCA
PheLeuAsnAlaGluAlaAsnLeuGlnAlaLeuIleAlaThrGlyGlyAspIleAsnAla 190       200       210       220       230       240
GCTATTGAAGCGTTACTGGGCTCCAGCCATCAGGAGGTGGAGGATCTGGAGGTGGAGTA
AlaIleGluAlaLeuLeuGlySerGlnProSerGlyGlyGlyGlySerGlyGlyGlyVal 250       260       270       280       290       300
AATCCTCAGCTACAGAATCCAGAAGTCGCGTTTCAGCAACAACTGGAACAACTCAGTGCA
AsnProGlnLeuGlnAsnProGluValAlaPheGlnGlnGlnLeuGluGlnLeuSerAla 310       320       330       340       350       360
ATGGGATTTTTGAACGCGGAAGCAAACTTGCAAGCTCTAATAGCAACAGGAGGTGATATT
METGlyPheLeuAsnAlaGluAlaAsnLeuGlnAlaLeuIleAlaThrGlyGlyAspIle 370       380       390       400       410       420
AATGCAGCTATTGAAGCGTTACTGGGCTCCAGCCATCAGGAGGTGGAGGATCTGGAGGT
AsnAlaAlaIleGluAlaLeuLeuGlySerGlnProSerGlyGlyGlyGlySerGlyGly 430       440       450       460       470       480
GGAGTAAATCCTCAGCTACAGAATCCAGAAGTCGCGTTTCAGCAACAACTGGAACAACTC
GlyValAsnProGlnLeuGlnAsnProGluValAlaPheGlnGlnGlnLeuGluGlnLeu 490       500       510       520       530       540
AGTGCAATGGGATTTTTGAACGCGGAAGCAAACTTGCAAGCTCTAATAGCAACAGGAGGT
SerAlaMETGlyPheLeuAsnAlaGluAlaAsnLeuGlnAlaLeuIleAlaThrGlyGly 550       560       570       580       590       600
GATATTAATGCAGCTATTGAAGCGTTACTGGGCTCCAGCCATCAGGAGGTGGAGGATCT
AspIleAsnAlaAlaIleGluAlaLeuLeuGlySerGlnProSerGlyGlyGlyGlySer 610       620       630       640       650       660
GGAGGTGGAGTAAATCCTCAGCTACAGAATCCAGAAGTCGCGTTTCAGCAACAACTGGAA
GlyGlyGlyValAsnProGlnLeuGlnAsnProGluValAlaPheGlnGlnGlnLeuGlu 670       680       690       700       710       720
CAACTCAGTGCAATGGGATTTTTGAACGCGGAAGCAAACTTGCAAGCTCTAATAGCAACA
GlnLeuSerAlaMETGlyPheLeuAsnAlaGluAlaAsnLeuGlnAlaLeuIleAlaThr 730       740       750       760       770       780
GGAGGTGATATTAATGCAGCTATTGAAGCGTTACTGGGCTCCAGCCATCAGGAGGTGGA
GlyGlyAspIleAsnAlaAlaIleGluAlaLeuLeuGlySerGlnProSerGlyGlyGly

790
GGATCGATCCCCTAG
GlySerIlePro***
```

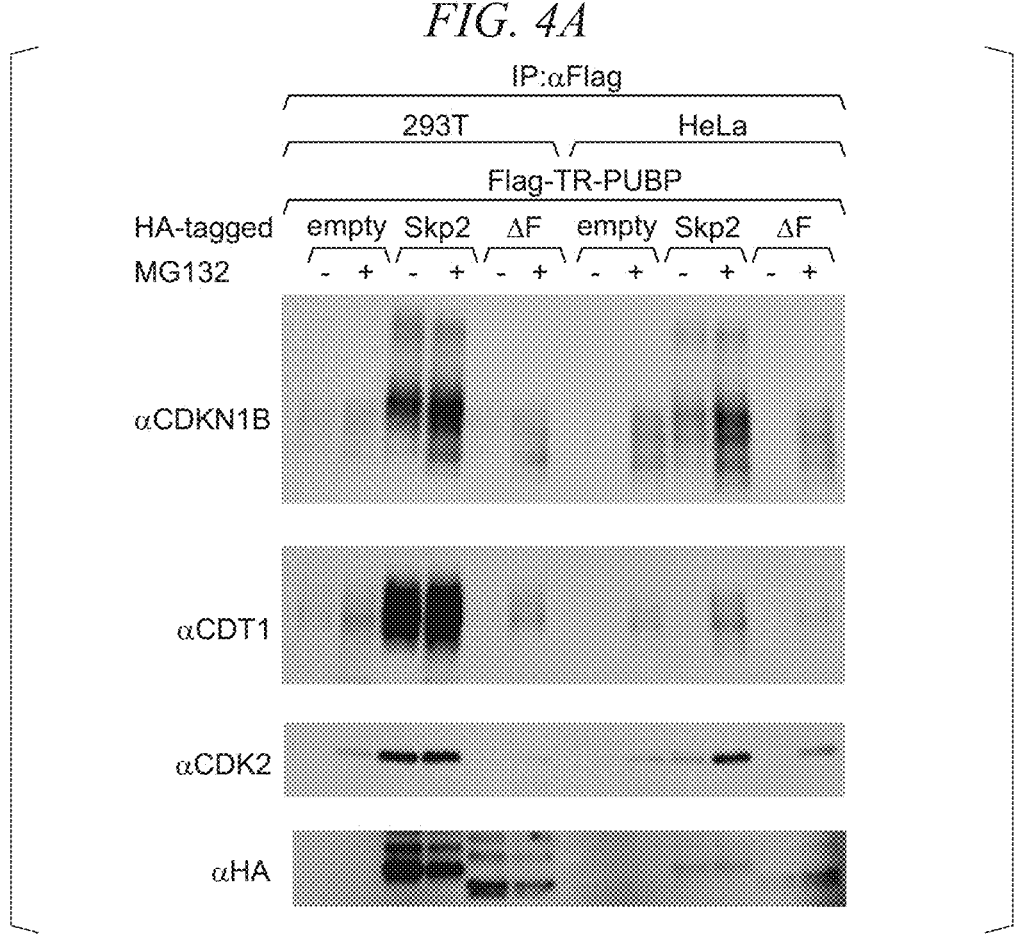
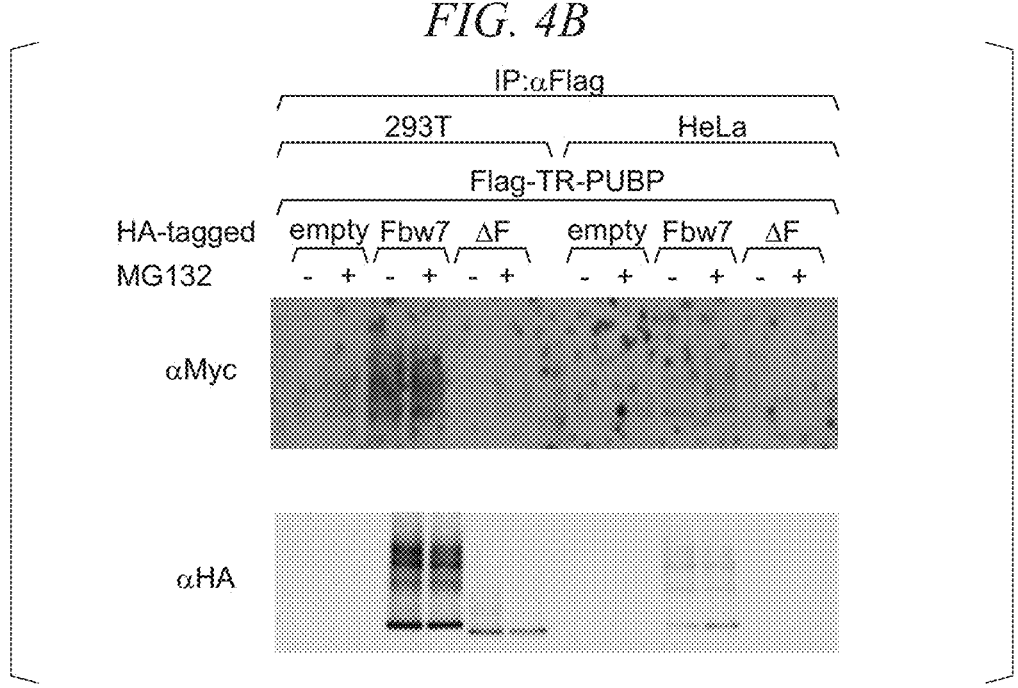

METHOD FOR IDENTIFYING POLYUBIQUITINATED SUBSTRATE

CROSS-REFERENCE TO RELATED APPLICATION

This application is a co-pending application which claims priority to PCT Application No. PCT/JP2014/080053, filed Nov. 13, 2014 and Japanese application No. 2013-237362, filed Nov. 15, 2013, herein incorporated by reference in their entirety.

SEQUENCE LISTING

This application contains a sequence listing filed in electronic form as an ASCII.txt file entitled 51966-1030_ST25.txt. The content of the sequence listing is incorporated herein in its entirety.

TECHNICAL FIELD

The present invention relates to a method for efficiently identifying a polyubiquitinated substrate.

BACKGROUND ART

Ubiquitin is a protein consisting of 76 amino acids present in all eukaryotes. By the action of three kinds of enzyme groups including E1 (ubiquitin-activating enzyme)/E2 (ubiquitin-conjugating enzyme)/E3 (ubiquitin ligase), glycine residues of the C-terminal of ubiquitins form isopeptide bonds mainly with lysine residues of a substrate protein. In many cases, polyubiquitin chains consisting of ubiquitins linked with other ubiquitins are formed and function as various posttranslational modification factors (for example, see Non-Patent Document 1 and Non-Patent Document 2). Among in vivo functions of the polyubiquitin chain, for example, a selective degradation system "ubiquitin-proteasome system" established by proteasome that tracks the polyubiquitin chain as a target is most widely known. In this system, the kind of protein that will be degraded and the timing the protein is degraded are important. That is, the selectivity of a substrate is important, and the selectivity depends on a ubiquitin ligase.

Human genes are encoded with about 600 kinds of ubiquitin ligases, but the substrates of very few ubiquitin ligases have been identified. Moreover, even if it is considered that in the ubiquitin ligases whose substrate has been identified, some uncharacterized substrates are highly likely to be found. In order to understand ubiquitination involved in the control of a wide range of biological phenomenon, it is important to develop a technique that makes it possible to comprehensively search for the substrate of ubiquitin ligases with a high level of sensitivity.

So far, as an approach for identifying ubiquitinated proteins, (1) a method of comprehensive analysis in which epitope-tagged ubiquitin is overexpressed in culture cells, and mass spectrometry is performed on the proteins having undergone immunoprecipitation by tag antibodies, (2) a method in which a mutant ubiquitin ligase not having ubiquitin ligase activity is expressed, and the binding proteins are comprehensively analyzed, and the like, have been adopted. In the method (1), the number of kinds of the ubiquitinated proteins that can be identified is extremely restricted. Presumably, this is because there may be a problem with the overexpression of ubiquitins. In the method (2), a large number of binding proteins which are not substrates are also identified, and accordingly, this method is inefficient as a method for identifying a substrate. In addition, as an affinity probe for the polyubiquitin chain, Tandem ubiquitin binding entities (TUBE) obtained by the fusion of four Ubiquitin-Associated (UBA) domains have been reported (for example, see Non-Patent Document 3).

Meanwhile, in recent years, an anti-diGly antibody has been developed and greatly contributes to the identification of ubiquitinated proteins (for example, see Non-Patent Document 4). For proteomic analysis, for example, a method of performing mass spectrometry on peptides that are obtained by trypsin digestion of sample proteins is generally used. Trypsin cleaves the C-terminal of lysine and arginine, but when ubiquitinated proteins are digested with trypsin, unique peptides having a sequence (ubiquitin signature) in which two glycine residues (diGly) have formed an isopeptide bond with a lysine residue as a ubiquitination site are formed. An antibody which recognizes the ubiquitin signature is the anti-diGly antibody.

PRIOR ART DOCUMENTS

[Non-Patent Document 1]
Komander and Rape, Annual review of biochemistry, 2012, vol. 81, p. 203-229
[Non-Patent Document 2]
Grabbe, et al., Nature reviews. Molecular cell biology, 2011, vol. 12, p. 295-307
[Non-Patent Document 3]
Hjerpe, et al., EMBO reports, 2009, vol. 10, p. 1250-1258
[Non-Patent Document 4]
Kim, et al., Molecular Cell, 2011, vol. 44, p. 325-340
[Non-Patent Document 5]
Frescas and Pagano, Nature Reviews Cancer, 2008, vol. 8, p. 438-449

DISCLOSURE OF THE INVENTION

Problems to be Solved by the Invention

Most of polyubiquitinated proteins are rapidly degraded by proteasome in vivo. Accordingly, it is generally difficult to identify the polyubiquitinated proteins. Moreover, the polyubiquitin chain is rapidly removed by a deubiquitinating enzyme (deubiquitination reaction). Consequently, even if the proteins are not degraded, it is not easy to isolate the proteins by immunoprecipitation or the like. For these reasons, with conventional methods, it is difficult to identify the ubiquitinated substrate.

An object of the present invention is to provide a method for efficiently identifying a polyubiquitinated substrate which is generally not easily identified.

Means for Solving the Problems

In order to achieve the above object, the present inventors conducted thorough research. As a result, they found that by expressing a trypsin-resistant polyubiquitin-chain binding protein (trypsin-resistant polyubiquitin chain probe) in a cell, the polyubiquitinated state of a substrate protein can be stabilized. They also found that by coexpressing the trypsin-resistant polyubiquitin chain probe and a ubiquitin ligase in a cell, a substrate that has been polyubiquitinated by the ubiquitin ligase can be efficiently isolated from the cell and identified. The present invention has been completed based on the findings.

That is, the method for identifying a polyubiquitinated substrate according to the present invention is described in the following [1] to [8].

[1] A method for identifying a polyubiquitinated substrate, comprising: (1) a step of expressing a trypsin-resistant polyubiquitin chain-binding protein and a ubiquitin ligase in a cell or in a cell lysate, (2) a step of isolating a complex that contains the trypsin-resistant polyubiquitin chain-binding protein from the cell or the cell lysate having undergone the step (1), (3) a step of subjecting the complex isolated by the step (2) to trypsin digestion, and (4) a step of identifying a peptide that has a ubiquitination site from a digested material obtained by the step (3).

[2] The method for identifying a polyubiquitinated substrate according to [1], further comprising: (1') a step of expressing the trypsin-resistant polyubiquitin chain-binding protein and a dominant-negative mutant of the ubiquitin ligase in another cell or another cell lysate of the same kind as the aforementioned cell or the cell lysate, (2') a step of isolating a complex that contains the trypsin-resistant polyubiquitin chain-binding protein from the cell or the cell lysate having undergone the step (1'), (3') a step of subjecting the complex isolated by the step (2') to trypsin digestion, (4') a step of identifying a peptide that has a ubiquitination site from the digested material obtained by the step (3'), and (5) a step of determining the peptide, which has been identified in the step (4) but has not been identified in the step (4'), is contained in a polyubiquitinated substrate.

[3] The method for identifying a polyubiquitinated substrate according to [1] or [2], in which the trypsin-resistant polyubiquitin chain-binding protein has two or more ubiquitin-binding domains that are linked with each other through a linker.

[4] The method for identifying a polyubiquitinated substrate according to [3], in which the trypsin-resistant polyubiquitin chain-binding protein has 4 to 8 ubiquitin-binding domains.

[5] The method for identifying a polyubiquitinated substrate according to [3] or [4], in which the ubiquitin-binding domains comprise an amino acid sequence that includes $18^{th}$ to $71^{st}$ amino acid residues in an amino acid sequence represented by SEQ ID NO:1.

[6] The method for identifying a polyubiquitinated substrate according to any one of [1] to [5], in which the trypsin-resistant polyubiquitin chain-binding protein has a polyubiquitin chain-binding site and a tag portion, and in the step (2), the complex is isolated by an immunoreaction using an antibody or a ligand that binds specifically to the tag portion in the trypsin-resistant polyubiquitin chain-binding protein.

[7] The method for identifying a polyubiquitinated substrate according to any one of [1] to [6], in which in the step (4), the peptide that has a ubiquitination site is identified after being selectively isolated and collected from the digested material obtained by the digestion step.

[8] The method for identifying a polyubiquitinated substrate according to [7], in which the peptide that has a ubiquitination site is selectively isolated and collected using an anti-diGly antibody.

Effects of the Invention

In the method for identifying a polyubiquitinated substrate according to the present invention, a trypsin-resistant polyubiquitin chain probe is used. Accordingly, a polyubiquitinated substrate, which is generally not easy to be stably isolated from a cell due to degradation or the like caused by proteasome, can be stably isolated in a state where the substrate has bound to a polyubiquitin chain. If the amino acid sequence of the stably isolated polyubiquitinated substrate is investigated, the polyubiquitinated substrate can be more efficiently identified compared to the case in which the conventional method is used.

BRIEF DESCRIPTION OF THE DRAWINGS

FIG. 2 is a view showing an amino acid sequence (SEQ ID NO:1) of Flag-TR-PUBP1 used in Reference Example 1 and a DNA sequence (SEQ ID NO:2) which encodes the amino acid sequence.

FIG. 4A shows the results that are obtained by performing western blotting, using an anti-CDKN1B antibody, an anti-CDT1 antibody, an anti-CDK2 antibody, and an anti-HA antibody, on anti-Flag antibody immunoprecipitates of coexpression product of TR-PUBP and Skp2 or the dominant-negative mutant thereof in Reference Example 2.

FIG. 4B shows the results that are obtained by performing western blotting, using an anti-Myc antibody and an anti-HA antibody, on anti-Flag antibody immunoprecipitates of coexpression product of TR-PUBP and Fbw7 or the dominant-negative mutant thereof in Reference Example 2.

BEST MODE FOR CARRYING OUT THE INVENTION

Figure 1A:
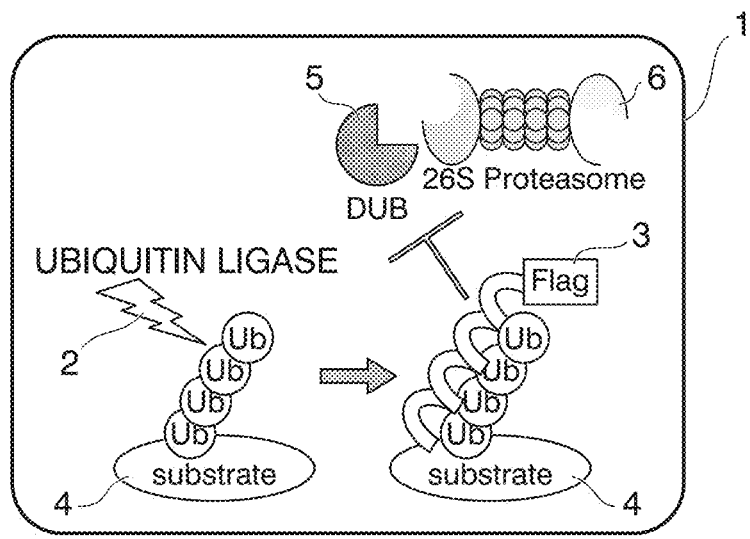
FIG. 1A is a view schematically showing that a polyubiquitinated substrate protein is protected by a trypsin-resistant polyubiquitin chain probe (TR-PUBP), when a ubiquitin ligase and a trypsin-resistant polyubiquitin chain probe are coexpressed in a cell, thereby protecting it from degradation by deubiquitinating enzyme (DUB) and 26S proteasome.
Figure 1B:
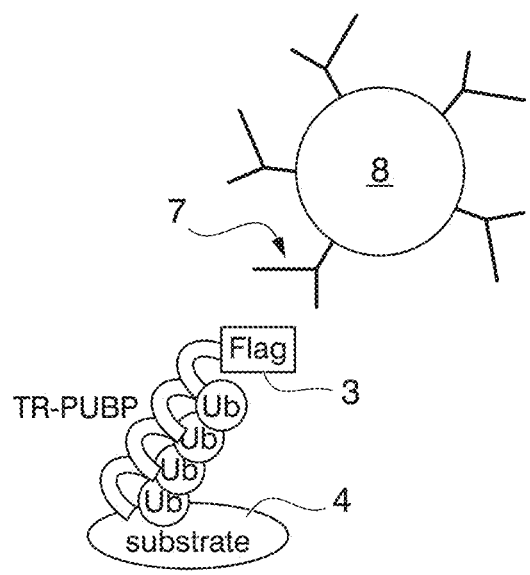
FIG. 1B is a view showing an embodiment in which polyubiquitinated protein to which TR-PUBP shown in FIG. 1A is bound is separated by immunoprecipitation using ant-FLAG antibodies.
Figure 1C:
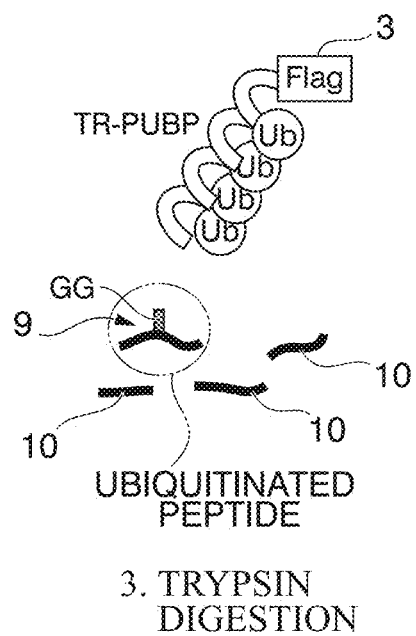
FIG. 1C is a schematic view showing the state of the polyubiquitinated protein separated by the immunoprecipitation and subjected to trypsin digestion.
Figure 1D:
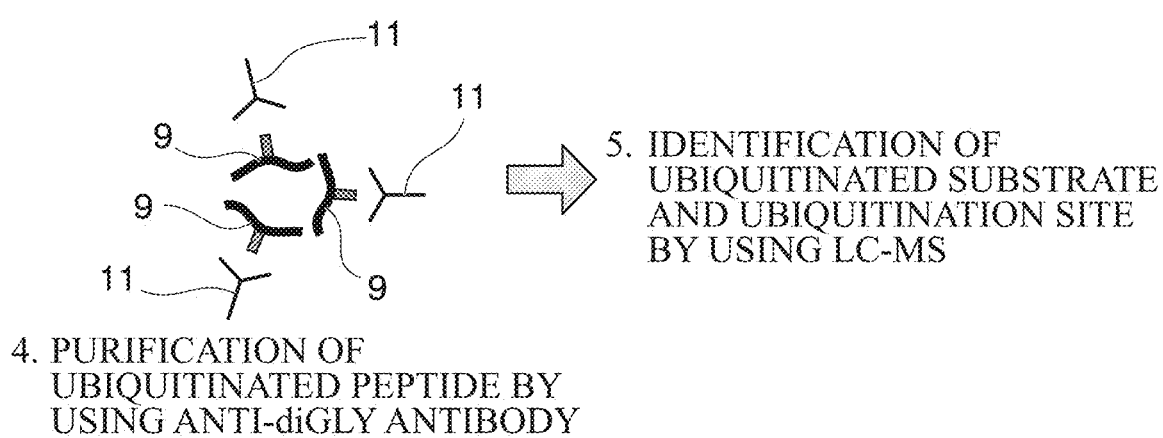
FIG. 1D is a schematic view showing a process of separating and collecting, using LC-MS, peptide containing ubiquitination sites in a selective way from polyubiquitinated protein subjected to trypsin digestion as shown in FIG. 1C.

The method for identifying a polyubiquitinated substrate according to the present invention (hereinafter, referred to as "identification method according to the present invention" in some cases) is a method for identifying a substrate that is polyubiquitinated by a specific ubiquitin ligase (hereinafter, referred to as "target ubiquitin ligase" in some cases). In the method, the target ubiquitin ligase and a trypsin-resistant polyubiquitin chain-binding protein (trypsin-resistant polyubiquitin chain probe, TR-PUBP) are coexpressed in a cell or a cell lysate. From the cell or the cell lysate in which both of the proteins are coexpressed, a complex comprising a polyubiquitinated protein and the TR-PUBP is isolated and collected, and then the polyubiquitinated protein is identified to be a polyubiquitinated substrate of the expressed target ubiquitin ligase. In the identification method according to the present invention, the target ubiquitin ligase as a target for identifying the substrate is expressed in a cell or a cell lysate, whereby polyubiquitination of the substrate protein of the ubiquitin ligase is accelerated. As a result, more polyubiquitinated substrate/TR-PUBP complexes are able to be isolated and collected, and accordingly, the polyubiquitinated substrate can be more efficiently identified. In addition, by coexpressing the TR-PUBP, it is possible to stably isolate the substrate polyubiquitinated by the ubiquitin ligase from the cell or the cell lysate expressing the target ubiquitin ligase, in a state where the substrate maintains the polyubiquitinated state.

Specifically, the identification method according to the present invention has the following steps (1) to (4):

(1) A step of expressing TR-PUBP and a ubiquitin ligase in a cell or a cell lysate;

(2) A step of isolating a complex containing the TR-PUBP from the cell or the cell lysate having undergone the step (1);

(3) A step of subjecting the complex isolated by the step (2) to trypsin digestion; and (4) A step of identifying a peptide containing a ubiquitination site from the digested material obtained by the step (3).

In the identification method according to the present invention, first, in the step (1), a target ubiquitin ligase as a target for identifying the substrate is coexpressed with TR-PUBP in a cell or a cell lysate. The target ubiquitin ligase may be a protein that has been confirmed to have ubiquitin ligase activity. Alternatively, the target ubiquitin ligase may be a protein that has not been confirmed in terms of whether or not it has ubiquitin ligase activity but is assumed to have ubiquitin ligase activity from the amino acid sequence thereof or the like.

The TR-PUBP used in the present invention may be a protein that has at least one trypsin-resistant ubiquitin-binding domain (TR-UBD). The TR-UBD is a domain of which basic amino acids such as arginine or lysine that are digested with trypsin are deleted or substituted with other amino acids, in a state where the domain retains a ubiquitin-binding ability. The TR-PUBP used in the present invention preferably has 2 or more TR-UBDs, more preferably has 4 or more TR-UBDs, and even more preferably has 4 to 8 TR-UBDs. When the TR-PUBP has 2 or more TR-UBDs, all of the TR-UBDs may be the same as each other (may have the same amino acid sequence), and the TR-PUBP may have a plurality of TR-UBDs.

The TR-UBD that the TR-PUBP has is not particularly limited as long as the TR-UBD is a domain having a ubiquitin-binding ability. For example, it is possible to use TR-UBDs that are formed by deletion or substitution of basic amino acids in UBDs such as a Ubiquitin Associated (UBA) domain, a Ubiquitin Interacting Motif (UIM), a Motif Interacting with Ubiquitin (MIU) domain, a double-sided ubiquitin-interacting motif (DUIM), a coupling of ubiquitin conjugation to ER degradation (CUE) domain, Np14 zinc finger (NZF), A20 zinc finger (ZnF), ubiquitin-specific processing protease zinc finger (UBP ZnF), ubiquitin-binding zinc finger (UBZ), ubiquitin-conjugating enzyme E2 variant (UEV), PLAA family ubiquitin binding (PFU), GRAM-like ubiquitin binding in EAP45 (GLUE), Golgi-localized, Gamma-ear-containing, Arf-binding (GAT), Jun kinase activation domain binding/Mpr1p and Pad1p N-termini (Jab/MPN), a Ubiquitin binding motif (UBM), and a ubiquitin-conjugating enzyme (Ubc).

When the TR-PUBP has 2 or more TR-UBDs, the respective TR-UBDs may be directly linked with each other. However, it is preferable for the TR-UBDs to be linked with each other through a flexible linker. Moreover, when the TR-PUBP has 3 or more TR-UBDs and has 2 or more linkers, the amino acid sequences of all of the linkers may be the same or different from each other. Examples of the amino acid sequences of the linker include a polyglycine sequence; a polyserine sequence; a sequence that is formed by substituting 1 or plural glycine residues in a polyglycine sequence with serine, threonine, alanine, proline, valine, glutamic acid, and the like; a sequence that is formed by substituting 1 or plural serine residues in a polyserine sequence with glycine, threonine, alanine, proline, valine, glutamic acid, and the like; and the like. The linker may be composed of 2 or more amino acid residues. However, the number of amino acid residues composing the linker is preferably 5 or more, more preferably 5 to 40, and even more preferably 5 to 20.

The TR-PUBP used in the present invention may have only a polyubiquitin chain-binding site (domain including a TR-UBD and a linker). However, it is preferable for the TR-PUBP to also have a tag portion. The tag portion may be positioned at the N-terminal or C-terminal site of the polyubiquitin chain-binding site. The tag portion and the polyubiquitin chain-binding site may be linked with each other directly or through appropriate linkers. When the TR-PUBP has the tag portion, if an immunoreaction using an antibody or a ligand which binds specifically to the tag portion is used, a complex comprising the polyubiquitinated substrate and the TR-PUBP can be more easily collected by being isolated from other components of the cell.

The tag portion can be used by being appropriately selected from tags that are generally provided to proteins. Examples of the tags include, but are not limited to, polypeptide tags such as a Flag tag, a hemagglutinin (HA) tag, a His tag, and a Myc tag, biotin, glutathione, dinitrophenol (DNP), digoxigenin, digoxin, glutathione-S-transferase (GST), a maltose-binding protein (MBP), avidin, streptavidin, and the like.

In the step (1), the cell in which the target ubiquitin ligase and the TR-PUBP are coexpressed is not particularly limited, as long as a ubiquitin which makes it possible for a polyubiquitin chain to be synthesized by the target ubiquitin ligase is expressed in the cell, and an independent expression system functions in the cell. The cell may be a prokaryotic cell (bacteria) such as E. coli or Bacillus subtilis or a eukaryotic cell such as yeast, fungus, an insect cell, or a mammal cell. Moreover, the cell may be a culture cell collected from a living organism or an artificially produced cell such as a cultured cell line. Furthermore, as cell lysate used for the coexpression of the target ubiquitin ligase and TR-PUBP, synthesis systems derived from a wheat germ, E. coli, rabbit reticulocytes, and insect cells can be used in the step (1).

The target ubiquitin ligase and the TR-PUBP can be coexpressed in a cell or a cell lysate by introducing an expression vector including a DNA sequence that encodes each of the proteins into the cell. As the expression vector, a plasmid vector, a virus vector, a cosmid vector, a BAC vector, a λ phage vector, and the like are known. The vector can be used by being appropriately selected from the vectors known in this technological field according to the type of cell to be introduced. In addition, the vectors obtained by modifying known vector by genetic recombination techniques may be used. The DNA sequence that encodes each of the proteins can be combined with the expression vector by using a known genetic recombination technique by means of a common method.

The expression vector can be introduced into a cell by a method that is appropriately selected from the methods known in this technological field in consideration of the type of expression vector and cell, and the like. Examples of the method of introducing a plasmid vector into a cell include an electroporation method, a calcium phosphate method, a liposome method, a DEAE dextran method, and the like. Moreover, a commercially available reagent for vector introduction may be used.

Next, in the step (2), from the cell or the cell lysate in which the target ubiquitin ligase and the TR-PUBP are co-expressed in the step (1), a complex containing the TR-PUBP is isolated. Specifically, for example, a cell lysate obtained by solubilizing the cell or the cell lysate having undergone the step (1) is brought into contact with solid-phase carriers having a site which binds specifically to the TR-PUBP, and then a solid-liquid separation is performed. By this method, the complex containing the TR-PUBP can be isolated from other components derived from the cell, in a state where the complex has bound to the solid-phase carriers. When the TR-PUBP has the aforementioned tag portion, solid carriers having directly or indirectly bound to an antibody or a ligand which binds specifically to the tag portion are added to the cell lysate, followed by incubation, and then the resultant is subjected to centrifugation or the like, whereby solid-liquid separation can be performed. Examples of the solid carriers include magnetic beads, nonmagnetic beads, a membrane filter, and the like. As the antibody or the like that binds specifically to the tag portion, the antibody or the like whose binding activity to the tag portion takes priority over the binding activity to other substances that are similar to the tag portion in terms of the physical or chemical properties, may be used. It is not necessary that the antibody or the like never binds to substances other than the tag portion.

Thereafter, in the step (3), the complex isolated by the step (2) is subjected to trypsin digestion. By the trypsin digestion, the polyubiquitin chain having bound to the TR-UBD does not degrade, but the substrate having bound to the polyubiquitin chain is fragmented. As a result, a polypeptide having a ubiquitin signature sequence that has diGly in a lysine residue as a ubiquitination site (site to which a ubiquitine has added) is produced. That is, the ubiquitination site is the lysine residue having bound to diGly by trypsin digestion.

Finally, in the step (4), a peptide having the ubiquitination site (lysine residue having bound to diGly) is identified from the digested material obtained by the step (3). The method for identifying the peptide is not particularly limited, and a method can be used by being appropriately selected from methods including mass spectrometry and the like that are generally used for identifying the amino acid sequence of a peptide.

The trypsin-digested materials also include many peptides not having the ubiquitination site.

Accordingly, if the peptide having the ubiquitination site is selectively isolated and collected from the trypsin-digested materials before each peptide is identified by proteomic analysis such as mass spectrometry, the peptide having the ubiquitination site can be efficiently identified. It is preferable for the peptide having the ubiquitination site to be isolated and collected by, for example, an immunoreaction using an anti-diGly antibody.

FIG. 1A to FIG. 1D schematically show an embodiment that includes a process of selectively isolating and collecting the peptide having the ubiquitination site from trypsin-digested materials by using an anti-diGly antibody in the identification method of the present invention. First, in a cell 1, a ubiquitin ligase 2 and a Flag-tagged TR-PUBP 3 are coexpressed (step (1) in FIG. 1A). By the ubiquitin ligase 2, a substrate 4 is polyubiquitinated. The Flag-tagged TR-PUBP 3 binds to the formed polyubiquitin chain. Accordingly, the polyubiquitin chain is stably present in the cell without being degraded by a deubiquitinating enzyme (DUB) 5 or a 26S proteasome 6. Subsequently, an anti-Flag antibody 7 having bound to a bead 8 is added to a cell lysate obtained by solubilizing the cell such that an immunoprecipitation reaction is caused by the anti-Flag antibody, whereby a ubiquitinated substrate is isolated (step (2) in FIG. 1B). Next, trypsin digestion is performed, whereby a peptide 9 having an ubiquitination site (lysine residue containing diGly) is produced (step (3) in FIG. 1C). By using an anti-diGly antibody 11, the peptide 9 having the ubiquitination site is collected by being isolated from a peptide 10 not having the ubiquitination site (step (4) in FIG. 1D). The purified (concentrated) peptide 9 having the ubiquitination site is identified by liquid chromatography-mass spectrometry (LC-MS) (step (5) in FIG. 1D).

Generally, a cell contains an intrinsic ubiquitin ligase. When the activity of the intrinsic ubiquitin ligase is extremely weaker than that of the target ubiquitin ligase in the cell in which the target ubiquitin ligase and the TR-PUBP are co-expressed, most of the peptides having the ubiquitination site that are identified by the step (4) are ones derived from polyubiquitinated substrates of the target ubiquitin ligase. On the contrary, when the intrinsic ubiquitin ligase exhibits sufficient activity, the peptides having the ubiquitination site that are identified by the step (4) also contain ones derived from polyubiquitinated substrates of the intrinsic ubiquitin ligase other than the target ubiquitin ligase. By expressing a dominant-negative mutant of the target ubiquitin ligase, it is possible to suppress the activity of the intrinsic target ubiquitin ligase which is expressed in the cell from the beginning. By utilizing the principle, the state at the time when a wild-type target ubiquitin ligase and the TR-PUBP are coexpressed is compared with the state at the time when the dominant-negative mutant and the TR-PUBP are coexpressed. In this manner, it is possible to more efficiently identify the polyubiquitinated substrate of the target ubiquitin ligase which is overexpressed, with effectively eliminating the influence of other intrinsic ubiquitin ligases corresponding to the target ubiquitin ligase. That is, when the amount of an immunoprecipitated protein becomes significantly greater in the expression of the wild type than in the expression of the dominant-negative mutant, the protein contains the polyubiquitinated substrate of the target ubiquitin ligase.

After a complex comprising the polyubiquitinated protein and the TR-PUBP is isolated and collected from the cell in which the target ubiquitin ligase and the TR-PUBP are coexpressed, the polyubiquitinated protein is identified. Moreover, after a complex comprising the polyubiquitinated protein and the TR-PUBP is isolated and collected from the cell in which the dominant-negative mutant of the target ubiquitin ligase and the TR-PUBP are coexpressed, the polyubiquitinated protein is identified independently of the above protein. The complex isolated from the cell, in which the dominant-negative mutant is coexpressed, contains a substrate protein that is polyubiquitinated by an intrinsic ubiquitin ligase other than the target ubiquitin ligase. Accordingly, among the peptides identified from the complex collected from the cell in which the target ubiquitin ligase is expressed, the peptide, which is not identified from the complex collected from the cell in which the dominant-negative mutant of the target ubiquitin ligase is expressed, contains the polyubiquitinated substrate of the target ubiquitin ligase. That is, when a group of peptides identified from the cell in which the dominant-negative mutant is coexpressed is excluded from a group of peptides identified from the cell in which the target ubiquitin ligase is coexpressed, the remaining peptides are contained in the polyubiquitinated substrates of the target ubiquitin ligase.

Specifically, in addition to the steps (1) to (4), the following steps (1') to (4') and (5) are performed.

(1') A step of expressing the trypsin-resistant polyubiquitin chain-binding protein and a dominant-negative mutant of the ubiquitin ligase in another cell or another cell lysate of the same kind as the aforementioned cell (2') A step of isolating a complex that contains the trypsin-resistant polyubiquitin chain-binding protein from the cell or the cell lysate having undergone the step (1')

(3') A step of subjecting the complex isolated by the step (2') to trypsin digestion (4') A step of identifying a peptide that has a ubiquitination site from the digested material obtained by the step (3'), and (5) A step of determining the peptide, which has been identified in the step (4) but has not been identified in the step (4'), is contained in a polyubiquitinated substrate For the cell in which only the TR-PUBP is expressed and the target ubiquitin ligase is not expressed, the peptide having the ubiquitination site can be identified by the same method as above, and the result can be compared with the results obtained from the cell in which the target ubiquitin ligase and the TR-PUBP are coexpressed. The peptide having the ubiquitination site that is identified in the cell in which only the TR-PUBP is expressed is highly likely to be a peptide fragment of the substrate of the intrinsic ubiquitin ligase. Therefore, the peptide having the ubiquitination site, which has been identified from the cell in which the target ubiquitin ligase and the TR-PUBP are coexpressed but has not been identified from the cell in which only the TR-PUBP is expressed, can be identified to be the peptide fragment of the substrate of the target ubiquitin ligase overexpressed in the cell.

As described above, by causing the polyubiquitinated substrate to form a complex with the TR-PUBP, it is possible to stably isolate and collect the polyubiquitinated substrate in a state where the substrate maintains the polyubiquitinated state. Accordingly, the TR-PUBP is also useful for screening of the polyubiquitinated substrate. For example, by performing the steps (1) and (2) in the identification method according to the present invention, it is possible to screen out the polyubiquitinated substrate from the cell. Moreover, the identification method itself according to the present invention can be used for screening of the polyubiquitinated substrate and for screening of candidate compounds that may be used as an agent for treating ubiquitin-related diseases.

Further, when the steps (1) and (1') are performed in an in vitro system, it is possible to identify the polyubiquitinated substrate in the same manner as above by using the ubiquitin ligase and the TR-PUBP. For example, a cell lysate containing the ubiquitin and the like, the ubiquitin ligase or the dominant-negative mutant thereof, and the TR-PUBP are added to a reaction solution, followed by incubation, whereby the substrate is polyubiquitinated, and a complex comprising the polyubiquitinated substrate and the TR-PUBP is formed. By performing the steps (2) to (4) or the steps (2) to (4) and (2') to (4') on the reaction solution containing the complex, the polyubiquitinated substrate of the ubiquitin ligase can be identified.

EXAMPLES

Hereinafter, the present invention will be described in more detail based on examples and reference examples, but the present invention is not limited to the following examples and the like.

Reference Example 1

<Preparation of Flag-TR-PUBP1 Expression Vector>

There are 3 arginine residues in UBA domain of UBQLN1 (NCBI accession number: Q9UMX0), and the residues are digested by trypsin. Therefore, a variant UBA domain obtained by substituting all of the arginine residues of the UBA domain with alanine residues was designed as a trypsin-resistant UBA (TR-UBA) domain (TR-UBD). Four TR-UBA domains described above were linked with one another through a flexible linker sequence (N-GGGSGGG-C) consisting of 7 amino acids, and a Flag tag was attached to the N-terminal. The protein obtained as above was named Flag-TR-PUBP1. FIG. 2 shows the amino acid sequence (SEQ ID NO:1) of the Flag-TR-PUBP1 and the DNA sequence (SEQ ID NO:2) encoding the protein. In FIG. 2, the domain surrounded by a solid line square indicates the TR-UBA domain, and the domain surrounded by a two-dot line square indicates the Flag tag (DYKDDDDK) (SEQ ID NO:3).

In the amino acid sequence represented by SEQ ID NO:1, the domain including the $18^{th}$ to $71^{st}$ amino acid residues, the domain including the $80^{th}$ to $133^{rd}$ amino acid residues, the domain including the $142^{nd}$ to $195^{th}$ amino acid residues, and the domain including the $204^{th}$ to $257^{th}$ amino acid residues are the TR-UBD. Moreover, the domain including the 72$^{nd}$ to 79$^{th}$ amino acid residues, the domain including the 134$^{th}$ to 141$^{st}$ amino acid residues, and the domain including the 196$^{th}$ to 203$^{rd}$ amino acid residues are the linker portion. In the present invention, the TR-PUBP is preferably a TR-PUBP in which UBDs including the 18$^{th}$ to 71$^{st}$ amino acid residues in the amino acid sequence represented by SEQ ID NO:1 are linked with each other through 2 or more linkers, and more preferably a TR-PUBP in which a tag has been attached to the N- or C-terminal thereof directly or through a linker.

A DNA fragment comprising a DNA sequence that encodes the Flag-TR-PUBP1 was inserted into a mammalian cell expression vector pc-DNA3, thereby preparing a Flag-TR-PUBP1 expression vector.

<Preparation of Flag-Ub Expression Vector>

A DNA fragment comprising a DNA sequence that encodes a protein (Flag-Ub) obtained by attaching a Flag tag to the N-terminal of a UBA domain of UBQLN1 (NCBI accession number: Q9UMX0) was inserted into a mammalian cell expression vector pcDNA3, thereby preparing a Flag-Ub expression vector.

<Preparation of HA-Skp2 Expression Vector>

A DNA fragment comprising a DNA sequence obtained by linking a DNA sequence that encodes a HA tag with the N-terminal of a DNA sequence that encodes a ubiquitin ligase Skp2 (NCBI accession number: Q9Z0Z3) was inserted into a mammalian cell expression vector pcDNA3, thereby preparing an HA-Skp2 expression vector.

<Transfection of Flag-TR-PUBP1 Expression Vector into Mammalian Culture Cell>

1.3×10$^6$ 293T cells or HeLa cells were seeded in a 10 cm φ dish and cultured for 24 hours in a $CO_2$ incubator at 37° C. by using Dulbecco's Modified Eagle's Medium (DMEM) supplemented with 10% by volume fetal bovine serum. The 293T cells were transfected with 3.5 µg of the Flag-TR-PUBP1 expression vector and 3.5 µg of the HA-Skp2 expression vector by using 21 µL of a polyethyleneimine (PEI) solution [1 mg/mL, linear (manufactured by Polysciences, Inc.), pH 7.4] and cultured for 48 hours. The HeLa cells were transfected with 2.5 µg of the Flag-TR-PUBP1 expression vector and 2.5 µg of the HA-Skp2 expression vector by using 30 µL of Lipofectamine and 21 µL of Plus reagent (manufactured by Life Technologies) and cultured for 24 hours.

As a control, instead of the HA-Skp2 expression vector, a HA-empty-vector obtained by inserting only a DNA fragment comprising a DNA sequence that encodes the HA tag into pcDNA3 was transfected into the 293T cells or HeLa cells in the same manner as above, and the cells were cultured.

The transfection was performed on 3 dishes for each sample. For culturing the cells, a proteasome inhibitor MG132 was added to 2 dishes among the 3 dishes such that the final concentration thereof stayed at 20 µm for 4 hours in the final stage of the culturing.

<Transfection of Flag-Ub Expression Vector into Mammalian Culture Cell>

The 293T cells or the HeLa cells were transfected and cultured in the same manner as above, except that the Flag-Ub expression vector was used instead of the Flag-TR-PUBP1 expression vector.

<Isolation of Polyubiquitinated Protein>

After the transfection, the culture supernatant of the cultured cells was removed, and the cells were taken by being scrapped with a cell scraper and transferred into a sample tube having a volume of 1.5 mL. Thereafter, the cells were collected by centrifugation performed for 3 minutes at 2,000 rpm, and the medium was removed. After the removal of the medium, 1 mL of PBS was added to the cells and the cells were suspended. Thereafter, the cells were collected by centrifugation performed for 3 minutes at 2,000 rpm, and the supernatant was removed. 1 mL of a protein extraction buffer (25 mM Tris-HCl, pH 7.5, 150 mM NaCl, 0.5% NP-40, complete-EDTA free (manufactured by Roche Ltd.)) cooled with ice was added to the collected cells, and the resultant was vigorously stirred using a vortex mixer and placed on ice for 10 minutes. Subsequently, the resultant was subjected to centrifugation for 20 minutes at 15,000 rpm, and the supernatant (whole cell lysate, WCL) was collected into a new sample tube having a volume of 1.5 mL. A portion of the collected supernatant was isolated so as to be used for a sample for SDS-PAGE electrophoresis and silver staining. Next, 6 µg of Dynabeads-ProteinG (manufactured by VERITAS Corporation) bonded to a DDDK antibody (anti-Flag antibody, FLA-1, manufactured by MBL, Co., Ltd.) was added to the remnant, and the resultant was gently mixed using a rotator for 30 minutes at 4° C., thereby causing immunoprecipitation of the Flag-tagged protein and the protein which binds thereto.

Among the respective samples, the WCL prepared from one of the two dishes supplemented with the proteasome inhibitor MG132 was supplemented with the DDDK antibody and a deubiquitinating enzyme inhibitor N-ethylmaleimide (NEM).

Thereafter, the beads having bound to the immunoprecipitate produced by the anti-Flag antibody were washed three times with 1 mL of TBS-N (25 mM Tris-HCl, pH 7.5, 150 mM NaCl) and then washed twice with 1 mL of 50 mM ammonium bicarbonate. After the supernatant was completely removed, 20 µL of a 200 µg/mL Flag peptide (manufactured by Sigma-Aldrich Co, LLC.) was added to the resultant, the beads were suspended, and then the resultant was left to standstill for 10 minutes. At this time, the beads were suspended by being tapped every 2 minutes. Subsequently, the supernatant was transferred to a new sample tube having a volume of 1.5 mL, and elution operation was repeated twice in the same manner as described above, thereby collecting 60 µL of an anti-Flag antibody immunoprecipitate solution. 10 µL of the solution and the WCL sample that had been isolated in advance were subjected to SDS-PAGE electrophoresis, followed by silver staining, western blotting using the DDDK antibody or an anti-ubiquitin antibody, and western blotting using an antibody against a substrate CDKN1B (NCBI accession number: P46527) of Skp2.

Figure 3A:
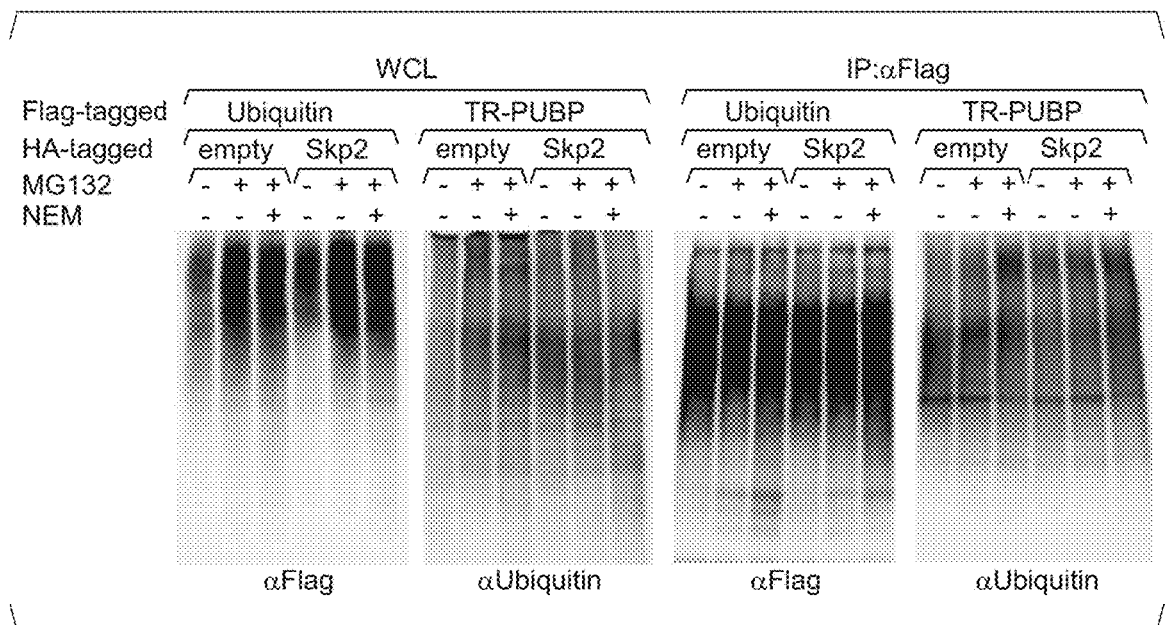
FIG. 3A is a view showing the results that are obtained by performing western blotting, using an anti-Flag antibody or an anti-ubiquitin antibody, on a whole cell lysate ("WCL" in the drawing) and an anti-Flag antibody immunoprecipitate solution ("IP: αFlag" in the drawing) of each sample in Reference Example 1.
Figure 3B:
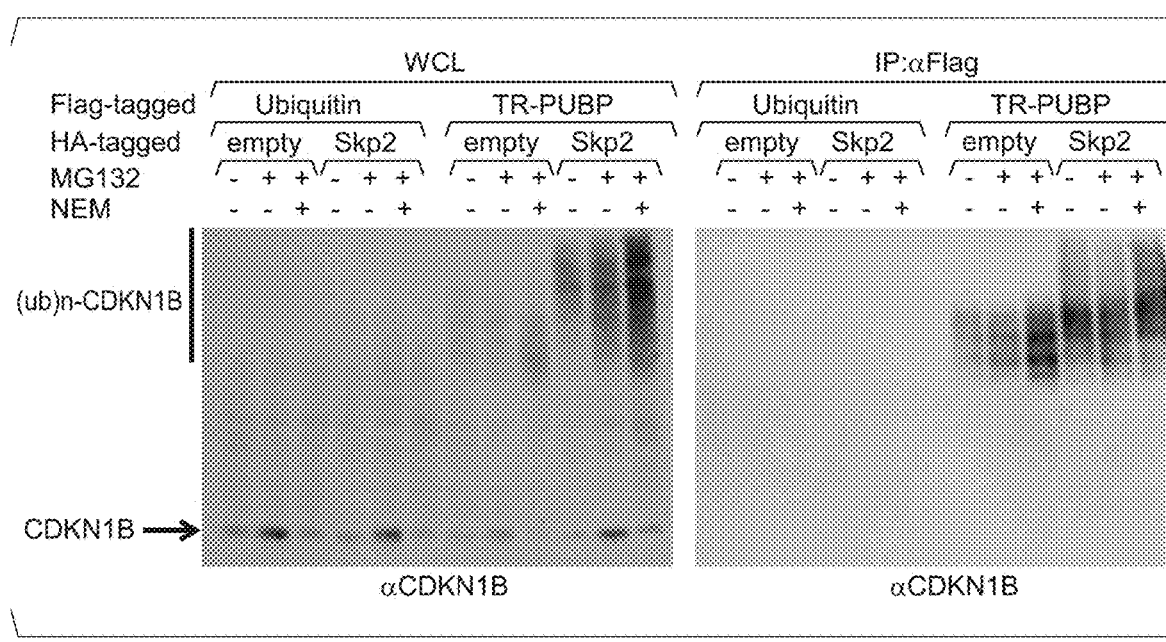
FIG. 3B is a view showing the results that are obtained by performing western blotting, using an anti-CDKN1B antibody, on whole cell lysates ("WCL" in the drawing) and anti-Flag antibody immunoprecipitates ("IP:αFlag" in the drawing) of each sample in Reference Example 1.

FIG. 3A shows the results obtained by western blotting performed using the DDDK antibody or the anti-ubiquitin antibody. The left panel of FIG. 3A shows the results obtained by using the whole cell lysate, and the right panel of FIG. 3A shows the results obtained by using the anti-Flag antibody immunoprecipitate solution. FIG. 3B shows the results obtained by western blotting performed using the antibody against the substrate CDKN1B of Skp2 in the same manner. The left panel of FIG. 3B shows the results obtained by using the whole cell lysate, and the right panel of FIG. 3B shows the results obtained by using the anti-Flag immunoprecipitate solution. In FIGS. 3A and 3B, "Ubiquitin" of "Flag-tagged" shows the results obtained from the cells transfected with the Flag-Ub expression vector, and "TR-PUBP" shows the results obtained from the cells transfected with the Flag-TR-PUBP1 expression vector. Moreover, "empty" of "HA-tagged" shows the results obtained from the cells transfected with the HA-empty-vector, and "Skp2" shows the results obtained from the cells transfected with the HA-Skp2 expression vector. In addition, in the column of "MG132" and "NEM", "+" shows the results obtained from the sample supplemented with each of the reagents, and "−" shows the results obtained from the sample not supplemented with the reagent. Furthermore, the antibody name described below the blots indicates the antibody used for western blotting, and "(Ub)n-CDKN1B" indicates the band of the polyubiquitinated CDKN1B.

By using the 293T cells, the conventional method of overexpressing a Flag-tagged ubiquitin (Flag-Ub) and a method of expressing Flag-TR-PUBP1 were compared to each other, in terms of the amount of the ubiquitinated proteins accumulated in a cell (FIG. 3A). It was found that the addition of the proteasome inhibitor MG132 or the deubiquitinating enzyme inhibitor NEM further increased the amount of the polyubiquitinated proteins in a cell (left panel of FIG. 3A). These polyubiquitinated proteins could be concentrated by immunoprecipitation of the overexpressed Flag-Ub or Flag-TR-PUBP1 (right panel of FIG. 3A).

It is widely known that the ubiquitin ligase Skp2 polyubiquitinates a CDK inhibitor protein CDKN1B (for example, see Non-Patent Document 5). Therefore, in order to examine effectiveness of the identification method according to the present invention, the following analysis was performed using Skp2:CDKN1B as a model case. First, by using the 293T cells, whether the polyubiquitinated CDKN1B is detected in immunoprecipitates of the Flag-Ub or Flag-TR-PUBP1 when the Skp2 is coexpressed was analyzed (right panel of FIG. 3B). As a result, in the immunoprecipitates in which the ubiquitin was overexpressed, the polyubiquitinated CDKN1B practically was not detected ($1^{st}$ to $6^{th}$ lanes of the right panel of FIG. 3B). On the contrary, in the immunoprecipitates of the Flag-TR-PUBP1, even in a state where the Skp2 was not overexpressed (indicated as "empty" in "HA-tagged") and the inhibitor was not added (indicated as "−" in both MG132 and NEM), the polyubiquitinated CDKN1B was detected ($7^{th}$ lane of the right panel of FIG. 3B). It is considered that this is because the expressed Flag-TR-PUBP1 binds to the CDKN1B ubiquitinated by the intrinsic Skp2, whereby degradation or deubiquitination is inhibited. When the Skp2 was coexpressed, the amount of the polyubiquitinated CDKN1B increased (compare the $7^{th}$ lane with the $10^{th}$ lane of the right panel of FIG. 3B). Moreover, in the whole cell lysate (WCL), accumulation of the polyubiquitinated CDKN1B was observed in the cells in which the Skp2 and the Flag-TR-PUBP1 were coexpressed ($10^{th}$ to $13^{th}$ lane in the left panel of FIG. 3B). From these results, it was understood that by the coexpression of the Flag-TR-PUBP1 and various ubiquitin ligases, the substrate of each ubiquitin ligase can be efficiently accumulated in the polyubiquitinated state.

Reference Example 2

As described in Reference Example 1, the TR-PUBP can cause the polyubiquitinated protein to be efficiently accumulated in a cell. Accordingly, in the immunoprecipitates of the Flag-TR-PUBP1, the proteins ubiquitinated by the intrinsic ubiquitin ligase are also concentrated (FIG. 3B). When the ubiquitin ligase was coexpressed, the substrate proteins were polyubiquitinated to a higher degree.

Therefore, inversely, by expressing the dominant-negative mutant of the ubiquitin ligase, whether the polyubiquitination of the substrate can be suppressed was analyzed.

<Preparation of HA-Skp2ΔF Expression Vector>

A DNA fragment comprising a DNA sequence obtained by linking a DNA sequence that encodes a HA tag with the N-terminal of a DNA sequence that encodes a dominant-negative mutant Skp2ΔF (SEQ ID NO:4) obtained by deleting a ubiquitin ligase activity domain from the ubiquitin ligase Skp2 (NCBI accession number: Q9Z0Z3) was inserted into a mammalian cell expression vector pcDNA3, thereby preparing an HA-Skp2ΔF expression vector.

<Preparation of HA-Fbw7 Expression Vector and HA-Fbw1 Expression Vector>

A DNA fragment consisting of a DNA sequence encoding the ubiquitin ligase Fbw7 (NCBI accession number: NM_033632) or ubiquitin ligase Fbw1 (NCBI accession number: NM_033637) to which a DNA sequence encoding HA tag is linked at the N-terminus thereof was introduced into an expression vector for mammalian cells, pcDNA3, to produce HA-Fbw7 expression vector and HA-Fbw1 expression vector, respectively.

<Preparation of HA-Fbw7ΔF Expression Vector and HA-Fbw1ΔF Expression Vector>

A DNA fragment consisting of a DNA sequence encoding the dominant negative mutant Fbw7ΔF (SEQ ID NO 5) or the dominant negative mutant Fbw1ΔF (SEQ ID NO 11), in which ubiquitin ligase active region of the ubiquitin ligase Fbw7 (NCBI accession number: Q969H0) or ubiquitin ligase Fbw1 (NCBI accession number: NM_033637) is deleted, and to which a DNA sequence encoding HA tag is linked at the N-terminus thereof was introduced into an expression vector for mammalian cells, pcDNA3, to produce HA-Fbw7ΔF expression vector and HA-Fbw1ΔF expression vector, respectively.

<Preparation of HA-MDM2 Expression Vector>

A DNA fragment consisting of a DNA sequence encoding the ubiquitin ligase (NCBI accession number: XM_0052688) to which a DNA sequence encoding HA tag is linked at the N-terminus thereof was introduced into an expression vector for mammalian cells, pcDNA3, to produce HA-MDM2 expression vector.

Figure 4C:
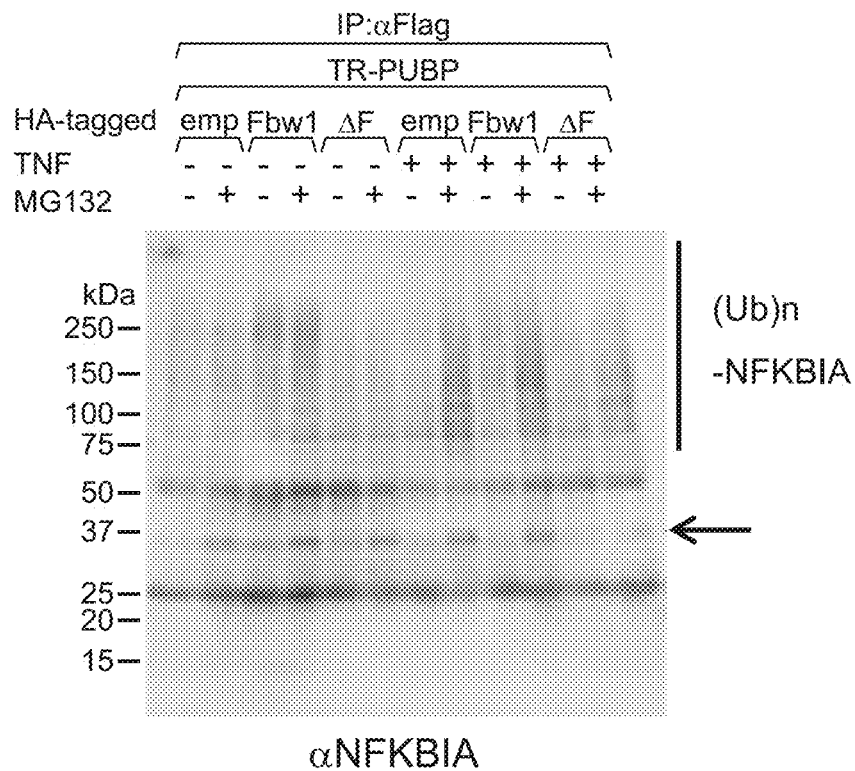
FIG. 4C shows the results that are obtained by performing western blotting, using an anti-NFKBIA antibody, on anti-Flag antibody immunoprecipitates of coexpression product of TR-PUBP and Fbw1 or the dominant-negative mutant thereof in Reference Example 2.
Figure 4D:
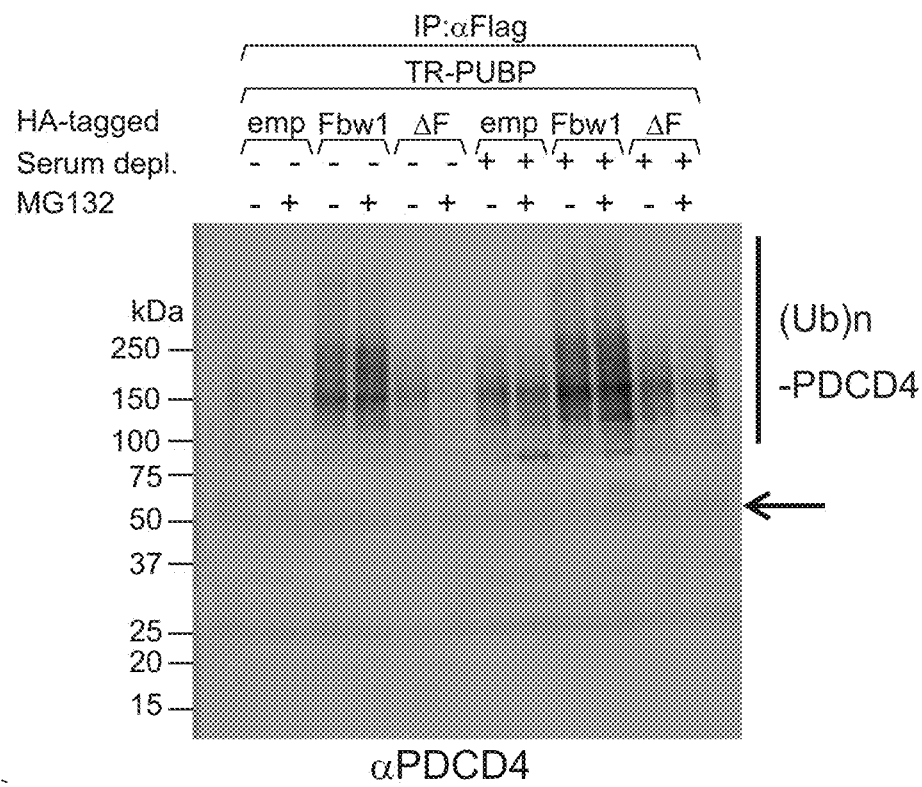
FIG. 4D shows the results that are obtained by performing western blotting, using an anti-PDCD4 antibody, on anti-Flag antibody immunoprecipitates of coexpression product of TR-PUBP and Fbw1 or the dominant-negative mutant thereof in Reference Example 2.
Figure 4E:
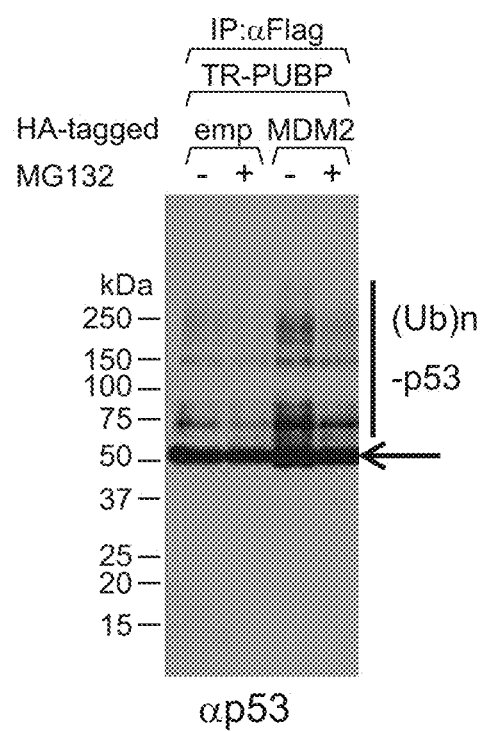
FIG. 4E shows the results that are obtained by performing western blotting, using an anti-p53 antibody, on anti-Flag antibody immunoprecipitates of coexpression product of TR-PUBP and MDM2 in Reference Example 2.

In the same manner as in Reference Example 1, the Flag-TR-PUBP1 expression vector, and the HA-empty-vector, the HA-Skp2 expression vector, or the HA-Skp2ΔF expression vector, HA-Fbw7 expression vector, HA-Fbw7ΔF vector, HA-Fbw1 expression vector, HA-Fbw1ΔF expression vector or HA-MDM2 expression vector were coexpressed in the 293T cells or the HeLa cells. The proteasome inhibitor MG132 was added such that the final concentration thereof stayed at 20 μM for 4 hours in the final stage of the culturing. Thereafter, in the same manner as in Reference Example 1, immunoprecipitates of the Flag-TR-PUBP1 were obtained using the DDDK antibody, the immunoprecipitates were subjected to electrophoresis, and western blotting was performed using an anti-CDKN1B antibody, an anti-CDT1 antibody, an anti-CDK2 antibody, an anti-HA antibody, an anti-cMyc antibody, an anti-NFKBIA antibody, an anti-PDCD4 antibody, or an anti-p53 antibody (in the cases in which an anti-NFKBIA antibody, an anti-PDCD4 antibody, or an anti-p53 antibody is used, only 293T cells were used). All of the anti-CDT1 antibody, the anti-CDK2 antibody, the anti-cMyc antibody, the anti-NFKBIA antibody, the anti-PDCD4 antibody, and the anti-p53 antibody are antibodies to the substrate of the ubiquitin ligase. The results are shown in FIG. 4A to FIG. 4E. In FIG. 4A, "empty" of "HA-tagged" shows the results obtained from the cells transfected with the HA-empty-vector, "Skp2" shows the results obtained from the cells transfected with the HA-Skp2 expression vector, and "ΔF" shows the results obtained from the cells transfected with the HA-Skp2ΔF expression vector, HA-Fbw7ΔF expression vector, or HA-Fbw1ΔF expression vector, respectively. Moreover, in the column of "MG132", "+" shows the results obtained from the sample supplemented with each of the reagents, and "−" shows the results obtained from the sample not supplemented with the reagent. Furthermore, the antibody names described in the column at the left side of the blots in FIG. 4A and FIG. 4B and the names described in the column at the bottom of the blot in FIG. 4C to FIG. 4E indicate the antibody used for western blotting. The results in FIG. 4C to FIG. 4E are the results obtained by using 293T cells.

In the 293T cells, the polyubiquitinated CDKN1B was detected in the immunoprecipitates of the cells in which only the Flag-TR-PUBP1 was expressed, even when the cells were not treated with the proteasome inhibitor (MG132) (first lane of FIG. 4A). On the contrary, the amount of the polyubiquitinated CDKN1B in the immunoprecipitates of the cells, in which the HA-Skp2 and the Flag-TR-PUBP1 were coexpressed, markedly increased. However, in the cells in which the dominant-negative mutant ("ΔF" in the drawing) was coexpressed, the polyubiquitinated CDKN1B practically was not detected. The same result was obtained from CDT1 (NCBI accession number: Q9H211) which is another known substrate of the Skp2. When the MG132 was added to the cells, the CDKN1B or the CDT1 was observed in the immunoprecipitates even if the dominant-negative mutant (ΔF) was expressed. Accordingly, it was considered that the difference between the ubiquitin ligase and the mutant thereof is more clearly observed when the cells are not treated with the MG132.

CDK2 (NCBI accession number: P24941) is a kinase protein that is known to directly bind to the CDKN1B or the Skp2. The protein showed the same behavior as that of the CDKN1B. However, the protein was detected not in the form of a polyubiquitinated protein but in the form of a single band. Therefore, it was understood that the immunoprecipitates contain not only polyubiquitinated proteins but also the proteins forming a complex with the polyubiquitinated proteins.

Next, regarding other ubiquitin ligases Fbw7, Fbw1, and MDM2; the polyubuiquitination of c-Myc (NCBI accession number: NM_002467), NFKBIA (NCBI accession number: NM_020529), PDCD4 (NCBI accession number: NM_014456), and p53 (NCBI accession number: NM_000546) which are known substrates of the ligases were analyzed in the same manner as described above. As a result, by the expression of the Flag-TR-PUBP1, the polyubiquitinated c-Myc, the polyubiquinated NFKBIA, the polyubiquinated PDCD4, and the polyubiquinated p53 were easily detected (FIG. 4B-FIG. 4E). Although it had been know that ubiquitination of the substrate of Fbw1 could be detected in response to the extracellular stimulus, a detection of the ubiquitination with a high sensitivity is possible even when the extracellular stimulus does not exist so long as the TR-PUBP1 system is used. In addition, in the case of an independent type of ubiquitin ligase MDM2, ubiquitination of a substrate was easily detected. This result indicates that the identification method according to the present invention can be applied to various ubiquitin ligases.

Moreover, from the above results, it was considered the strategy for identifying a polyubiquitinated substrate by means of comparing the 293T cell, in which the Flag-TR-PUBP1 and a ubiquitin ligase are co-expressed, with the cell, in which the Flag-TR-PUBP1 and a dominant-negative mutant of the ubiquitin ligase are co-expressed, in terms of the protein contained in the immunoprecipitate of each cell is convenient and effective as a screening method for substrate identification.

Example 1

Based on the results obtained as above, the proteins that were immunoprecipitated from the cells, in which the Flag-TR-PUBP1 was expressed, by using the anti-Flag antibody and degraded by trypsin were subjected to mass spectrometry, thereby identifying the peptide having the ubiquitination site.

<Trypsin Digestion>

5 μL of 50 mM Tris (2-carboxy-ethyl)phosphine hydrochloride (manufactured by Sigma-Aldrich Co, LLC.) was added to 50 μL of the remnant of the anti-Flag antibody immunoprecipitate solution of each sample prepared in Reference Example 1, and the resultant was heated for 30 minutes at 60° C. Thereafter, 2.5 μL of 200 mM Methyl Methanethiosulphoate (manufactured by Wako Pure Chemical Industries, Ltd.) was added thereto, and the solution was left at room temperature for 10 minutes. Subsequently, 50 μg of Trypsin Gold (manufactured by Promega Corporation) was added to the solution to cause a reaction for 16 hours at 37° C., thereby obtaining a trypsin digested material.

<Purification of diGly Peptide>

20 μL of 25× complete-EDTA free and 102.5 μL of pure water were added to the trypsin digested material, and 20 μL of 10× IAP Buffer included in a PTMScan Ubiquitin Remnant Motif (K-ε-GG) kit (manufactured by Cell Signaling Technology, Inc.) was added to the solution. Thereafter, 15 μL of PTMScan Ubiquitin Remnant Motif (K-ε-GG) antibody Bead Conjugate (anti-diGly antibody-binding beads) that had been washed with PBS in advance was added to 200 μL of the solution, and the resultant was gently mixed for 2 hours at 4° C. by using a rotator. Subsequently, the beads were washed twice with 1× IAP Buffer and then washed three times with pure water. After the supernatant was completely removed, peptides were extracted three times from the beads by using 20 μL of 0.15% trifluoroacetic acid.

<Mass Spectrometry>

The peptides, which were purified from the obtained extract (purified diGly peptides) by using a C18 column such as ZipTip (manufactured by Millipore Corporation) or StageTips (manufactured by Thermo Fisher Scientific Inc.), were analyzed by mass spectrometry. The mass spectrometry was performed using a mass spectrometer (nano-LC-HRMS: manufactured by Thermo Fisher Scientific Inc., Q-exactive).

From the 293T cell in which the Flag-TR-PUBP1 and the HA-Skp2 were expressed, 2300 proteins were identified. When the proteins, which were not detected in the cell in which the Skp2ΔF as a dominant-negative mutant was expressed or were detected in a markedly trace amount, were excluded from the above proteins, about 90 proteins remained. These proteins contained seven known substrates and a large number of binding factors (such as CDK2) thereof. Likewise, from the HeLa cell, 1788 proteins were identified. In the anti-Flag antibody immunoprecipitates obtained from the cell in which the wild-type Skp2 was expressed, about 61 proteins were confirmed. Among these proteins, 7 proteins were the substrates that have already been reported as substrates ubiquitinated by the Skp2.

Next, a peptide mixture, which was obtained by subjecting the anti-Flag antibody immunoprecipitates to trypsin digestion and causing immunoprecipitation of the resultant by using the anti-diGly antibody, was analyzed by mass spectrometry. From the 293T cell in which the Flag-TR-PUBP1 and the HA-Skp2 were expressed, 932 peptides were finally identified with high certainty. Among these, 902 proteins had diGly which is a ubiquitin signature and grouped into 332 proteins. Fifteen among these were the proteins that were not detected when the dominant-negative mutant (ΔF) of the Skp2 was expressed. These proteins included 3 known substrates such as CDT1, CDKN1B, and CDKN1A, and these substrates were confirmed to be ubiquitinated in western blotting. The amino acid sequence of the peptide of CDT 1 that included the diGly sequence was IAPPK[di-GlyGly]LAC[methylthio]R (SEQ ID NO:6); the amino acid sequence of the peptide of CDKN1B that included the diGly sequence was K[di-GlyGly]RPATDDSSTQNK[di-GlyGly]R (SEQ ID NO:7); and the amino acid sequence of the peptide of CDKN1A that included the diGly sequence was QTSM[Oxid]TDFYHSK[di-GlyGly]R (SEQ ID NO:8).

Figure 5A:
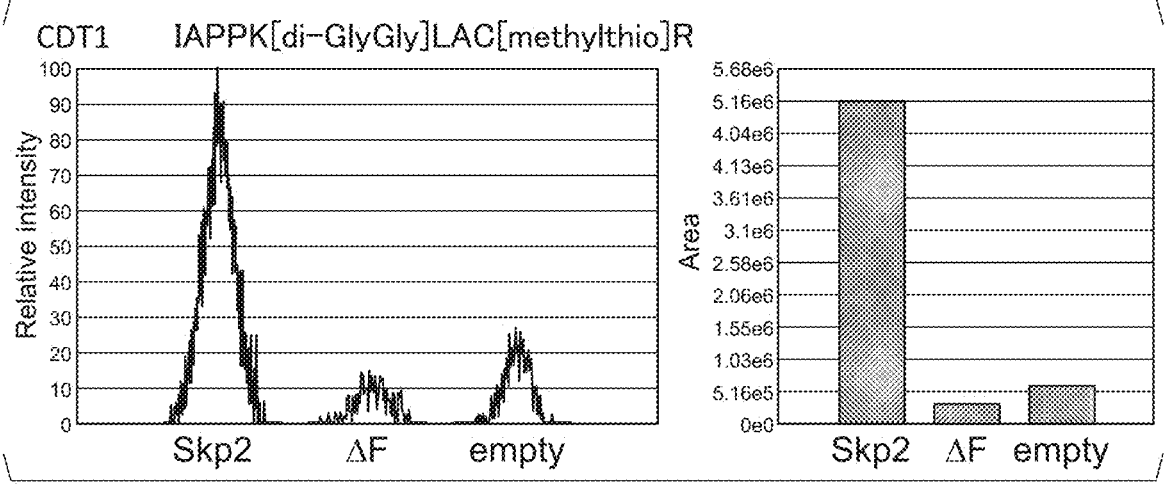
FIG. 5A is a view showing the results that are obtained by performing quantitative analysis on peptides having a diGly sequence of CDT 1 in Example 1.
Figure 5B:
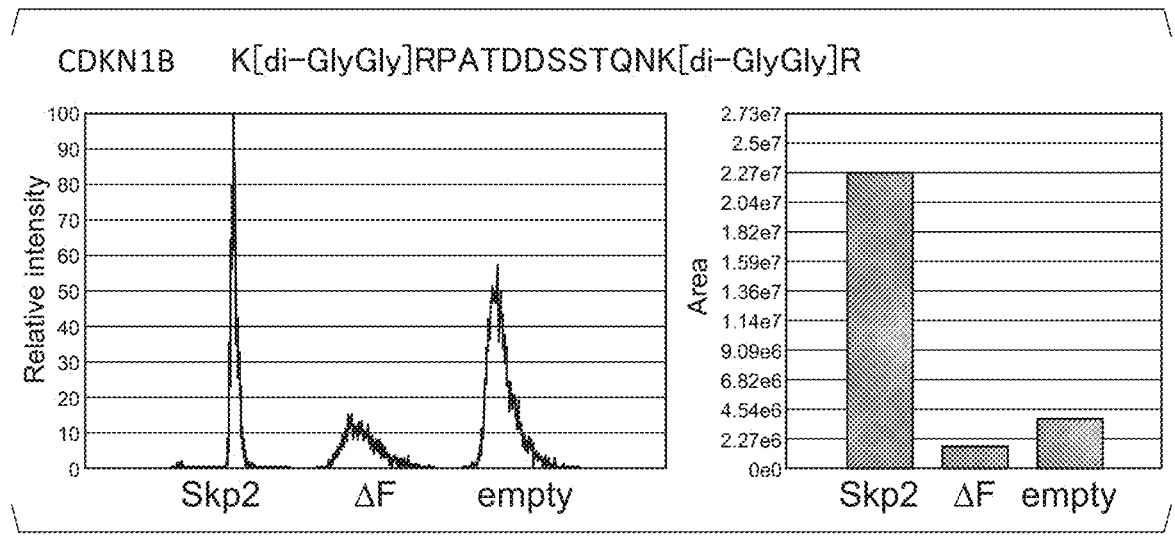
FIG. 5B is a view showing the results that are obtained by performing quantitative analysis on peptides having a diGly sequence of CDKN1B in Example 1.
Figure 5C:
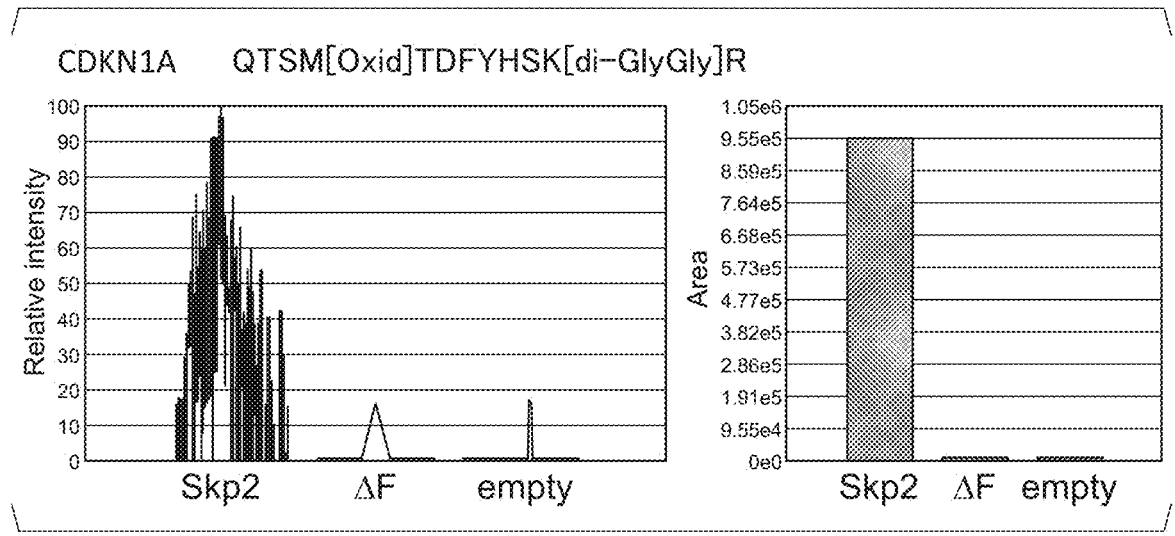
FIG. 5C is a view showing the results that are obtained by performing quantitative analysis on peptides having a diGly sequence of CDKN1A in Example 1.

The quantitative ratio among the identified peptides of the known substrates that include the diGly sequence was determined by quantitative analysis by using PinPoint (manufactured by Thermo Fisher Scientific Inc.). FIG. 5A shows the result of the quantitative analysis performed on the peptide of CDT1 that includes the diGly sequence; FIG. 5B shows the result of the quantitative analysis performed on the peptide of CDKN1B that includes the diGly sequence; and FIG. 5C shows the results of the quantitative analysis performed on the peptide of CDKN1A that includes the diGly sequence, respectively. In FIGS. 5A to 5C, the right panel shows the result obtained by quantitating the peak area of the left panel. These 3 kinds of known substrates reflect the results of western blotting. From the result, it was understood that the amount of the substrates significantly increases by overexpression of the Skp2. Regarding other candidate proteins, by obtaining antibodies against the proteins and performing western blotting, polyubiquitination of the proteins can be confirmed.

Example 2

Instead of the Skp2, F-box protein Fbxo21 (NCBI accession number: O94952) of which the function is unknown and which is expressed in many organs and cells was used to search for new polyubiquitinated substrates in the same manner as in Example 1.

<Preparation of Fbxo21 Expression Vector>

A DNA fragment comprising a DNA sequence obtained by linking a DNA sequence that encodes a HA-tag with the N-terminal of a DNA sequence that encodes the F-box protein Fbxo21 was inserted into the mammalian cell expression vector pcDNA3, thereby preparing an HA-Fbxo21 expression vector.

<Preparation of HA-Fbxo21ΔF Expression Vector>

A DNA fragment comprising a DNA sequence obtained by linking a DNA sequence that encodes a HA tag with the N-terminal of a DNA sequence that encodes a dominant-negative mutant Fbxo21ΔF (SEQ ID NO:9) obtained by deleting a domain assumed to be as a ubiquitin ligase activity domain of the Fbxo21 was inserted into the mammalian cell expression vector pcDNA3, thereby preparing an HA-Fbxo21ΔF expression vector.

In the same manner as in Reference Example 1, the Flag-TR-PUBP1 expression vector and the HA-empty vector, the HA-Fbxo21 expression vector, or the HA-Fbxo21ΔF expression vector were coexpressed in the 293T cell. The proteasome inhibitor MG132 was added such that the final concentration thereof stayed at 20 μM for 4 hours in the final stage of culturing. Thereafter, in the same manner as in Reference Example 1, an anti-Flag antibody immunoprecipitate solution was obtained using the DDDK antibody.

Subsequently, in the same manner as in Example 1, the anti-Flag antibody immunoprecipitate solution of each sample was subjected to trypsin digestion, and diGly peptides were purified from the obtained trypsin digested material. Thereafter, the peptides which were purified from the purified diGly peptides by using a C18 column were analyzed by mass spectrometry. As a result, several proteins were identified to be polyubiquitinated substrates.

Figure 6:
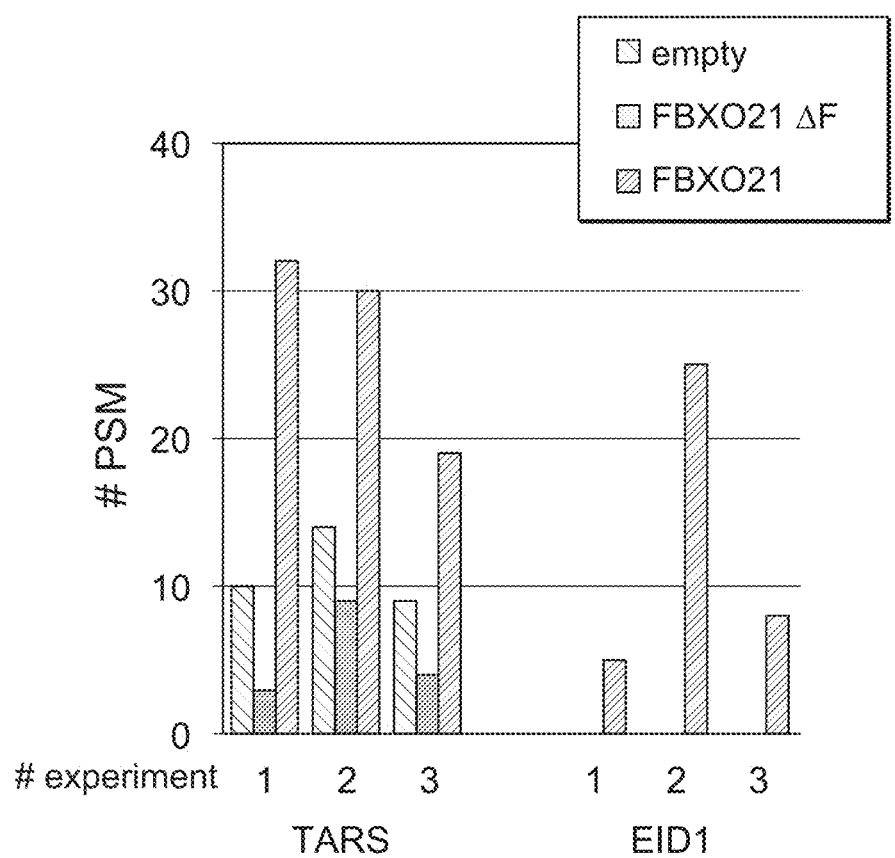
FIG. 6 is a view showing the results that are obtained by performing quantitative analysis on a peptide having a diGly sequence of TRAS and EID1 in Example 2.

The quantitative ratio among the identified peptides including the diGly sequence was determined in the same manner as in Example 1 by quantitative analysis by using PinPoint (manufactured by Thermo Fisher Scientific Inc.). As new substrates, TARS (NCBI accession number: NM_152295) and EID1 (NCBI accession number: NM 014335) were identified. FIG. 6 shows the results of quantitative analysis performed on the peptide of TARS that includes the diGly sequence. The amino acid sequence of TARS that included the diGly sequence was ILNEK[di-GlyGly]VNTPTTTVYR (SEQ ID NO:10), NSSTYWEGK[di-GlyGly]ADMETLQR (SEQ ID NO:12), FQEEAK[di-GlyGly]NR (SEQ ID NO:13), and HTGK[di-GlyGly]IK (SEQ ID NO:14), and the amino acid sequence of EID1 that included the diGly sequence was VSAALEEADK[di-GlyGly]M[Oxid]FLR (SEQ ID NO:15), and SGAQQLEEEGPM[Oxid]EEEEAQPM[Oxid]AAPEGK[di-GlyGly]R (SEQ ID NO:16). In FIG. 6, the right view shows the result obtained by quantitating the area of the left view. From the result, it was understood that the amount of the peptide of TARS that includes the diGly sequence is reduced by overexpression of the Fbxo21ΔF compared to the case where the empty vector is expressed, and the amount is significantly increased by overexpression of the Fbxo21. The trend of the quantitative ratio among the peptides of the TARS that include the diGly sequence is the same as that of the CDT1 and the like observed in the case where the Skp2 is expressed. Accordingly, the Fbxo21 is highly likely to be a ubiquitin ligase, and the TARS is highly likely to be a polyubiquitinated substrate of the Fbxo21. These results clearly show that the identification method according to the present invention makes it possible to efficiently identify new polyubiquitinated substrates.

EXPLANATION OF REFERENCES

1: cell 2: ubiquitin ligase Ub: ubiquitin 3: Flag-tagged TR-PUBP 4: substrate 5: deubiquitinating enzyme (DUB) 6: 26S proteasome 7: anti-Flag antibody 8: bead 9: peptide having the ubiquitination site 10: peptide not having the ubiquitination site 11: anti-diGly antibody

We claim:

1. A method for identifying a polyubiquitinated substrate, comprising:
   (1) a step of co-expressing a trypsin-resistant polyubiquitin chain-binding protein and a ubiquitin ligase in a cell or a cell lysate;
   (2) a step of isolating a complex that contains the trypsin-resistant polyubiquitin chain-binding protein from the cell or the cell lysate having undergone the step (1);
   (3) a step of subjecting the complex isolated by the step (2) to trypsin digestion; and
   (4) a step of identifying a peptide that has a ubiquitination site from a digested material obtained by the step (3).

2. The method for identifying a polyubiquitinated substrate according to claim 1, further comprising:
   (1') a step of co-expressing the trypsin-resistant polyubiquitin chain-binding protein and a dominant-negative mutant of the ubiquitin ligase in another cell or another cell lysate of the same kind as the aforementioned cell;
   (2') a step of isolating a complex that contains the trypsin-resistant polyubiquitin chain-binding protein from the cell or the cell lysate having undergone the step (1');
   (3') a step of subjecting the complex isolated by the step (2') to trypsin digestion;
   (4') a step of identifying a peptide that has a ubiquitination site from the digested material obtained by the step (3'); and
   (5) a step of determining the peptide, which has been identified in the step (4) but has not been identified in the step (4'), is contained in a polyubiquitinated substrate.

3. The method for identifying a polyubiquitinated substrate according to claim 1,
   wherein the trypsin-resistant polyubiquitin chain-binding protein has two or more ubiquitin-binding domains that are linked with each other through a linker.

4. The method for identifying a polyubiquitinated substrate according to claim 3, wherein the trypsin-resistant polyubiquitin chain-binding protein has 4 to 8 ubiquitin-binding domains.

5. The method for identifying a polyubiquitinated substrate according to claim 3,
wherein the ubiquitin-binding domains comprise an amino acid sequence that includes $18^{th}$ to $71^{st}$ amino acid residues in an amino acid sequence represented by SEQ ID NO:1.

6. The method for identifying a polyubiquitinated substrate according to claim 1,
wherein the trypsin-resistant polyubiquitin chain-binding protein has a polyubiquitin chain-binding site and a tag portion, and
in the step (2), the complex is isolated by an immunoreaction using an antibody or a ligand that binds specifically to the tag portion in the trypsin-resistant polyubiquitin chain-binding protein.

7. The method for identifying a polyubiquitinated substrate according to claim 1,
wherein in the step (4), the peptide that has a ubiquitination site is identified after being selectively isolated and collected from the digested material obtained by the digestion step.

8. The method for identifying a polyubiquitinated substrate according to claim 7,
wherein the peptide that has a ubiquitination site is selectively isolated and collected using an anti-diGly antibody.

* * * * *

SEQUENCE LISTING

<160> NUMBER OF SEQ ID NOS: 16

<210> SEQ ID NO 1

```
<211> LENGTH: 264
<212> TYPE: PRT
<213> ORGANISM: Artificial Sequence
<220> FEATURE:
<223> OTHER INFORMATION: Description of Artificial Sequence:
      FLAG-TR-PUBP1

<400> SEQUENCE: 1
```

Met Asp Tyr Lys Asp Asp Asp Lys Gly Ile Ile Arg Ser Gly Gly
1               5                   10                  15

Gly Val Asn Pro Gln Leu Gln Asn Pro Glu Val Ala Phe Gln Gln Gln
            20                  25                  30

Leu Glu Gln Leu Ser Ala Met Gly Phe Leu Asn Ala Glu Ala Asn Leu
        35                  40                  45

Gln Ala Leu Ile Ala Thr Gly Gly Asp Ile Asn Ala Ala Ile Glu Ala
    50                  55                  60

Leu Leu Gly Ser Gln Pro Ser Gly Gly Gly Ser Gly Gly Gly Val
65                  70                  75                  80

Asn Pro Gln Leu Gln Asn Pro Glu Val Ala Phe Gln Gln Gln Leu Glu
                85                  90                  95

Gln Leu Ser Ala Met Gly Phe Leu Asn Ala Glu Ala Asn Leu Gln Ala
            100                 105                 110

Leu Ile Ala Thr Gly Gly Asp Ile Asn Ala Ala Ile Glu Ala Leu Leu
        115                 120                 125

Gly Ser Gln Pro Ser Gly Gly Gly Ser Gly Gly Gly Val Asn Pro
    130                 135                 140

Gln Leu Gln Asn Pro Glu Val Ala Phe Gln Gln Gln Leu Glu Gln Leu
145                 150                 155                 160

Ser Ala Met Gly Phe Leu Asn Ala Glu Ala Asn Leu Gln Ala Leu Ile
                165                 170                 175

Ala Thr Gly Gly Asp Ile Asn Ala Ala Ile Glu Ala Leu Leu Gly Ser
            180                 185                 190

Gln Pro Ser Gly Gly Gly Ser Gly Gly Gly Val Asn Pro Gln Leu
        195                 200                 205

Gln Asn Pro Glu Val Ala Phe Gln Gln Gln Leu Glu Gln Leu Ser Ala
    210                 215                 220

Met Gly Phe Leu Asn Ala Glu Ala Asn Leu Gln Ala Leu Ile Ala Thr
225                 230                 235                 240

Gly Gly Asp Ile Asn Ala Ala Ile Glu Ala Leu Leu Gly Ser Gln Pro
                245                 250                 255

Ser Gly Gly Gly Gly Ser Ile Pro
            260

```
<210> SEQ ID NO 2
<211> LENGTH: 795
<212> TYPE: DNA
<213> ORGANISM: Artificial Sequence
<220> FEATURE:
<223> OTHER INFORMATION: Description of Artificial Sequence:
      FLAG-TR-PUBP1

<400> SEQUENCE: 2
atggactaca aggacgacga tgacaagggg atcatcagat ctggaggtgg agtaaatcct      60
cagctacaga atccagaagt cgcgtttcag caacaactgg aacaactcag tgcaatggga     120
tttttgaacg cggaagcaaa cttgcaagct ctaatagcaa caggaggtga tattaatgca     180
gctattgaag cgttactggg ctcccagcca tcaggaggtg gaggatctgg aggtggagta     240
```

```
aatcctcagc tacagaatcc agaagtcgcg tttcagcaac aactggaaca actcagtgca    300
atgggatttt tgaacgcgga agcaaacttg caagctctaa tagcaacagg aggtgatatt    360
aatgcagcta ttgaagcgtt actgggctcc cagccatcag gaggtggagg atctggaggt    420
ggagtaaatc ctcagctaca gaatccagaa gtcgcgtttc agcaacaact ggaacaactc    480
agtgcaatgg gattttgaa cgcggaagca aacttgcaag ctctaatagc aacaggaggt    540
```

```
aatcctcagc tacagaatcc agaagtcgcg tttcagcaac aactggaaca actcagtgca    300
atgggatttt tgaacgcgga agcaaacttg caagctctaa tagcaacagg aggtgatatt    360
aatgcagcta ttgaagcgtt actgggctcc cagccatcag gaggtggagg atctggaggt    420
ggagtaaatc ctcagctaca gaatccagaa gtcgcgtttc agcaacaact ggaacaactc    480
agtgcaatgg gattttgaa cgcggaagca aacttgcaag ctctaatagc aacaggaggt    540
gatattaatg cagctattga agcgttactg ggctcccagc catcaggagg tggaggatct    600
ggaggtggag taaatcctca gctacagaat ccagaagtcg cgtttcagca acaactggaa    660
caactcagtg caatgggatt tttgaacgcg gaagcaaact tgcaagctct aatagcaaca    720
ggaggtgata ttaatgcagc tattgaagcg ttactgggct cccagccatc aggaggtgga    780
ggatcgatcc cctag                                                    795
```

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Flag tag

<400> SEQUENCE: 3

Asp Tyr Lys Asp Asp Asp Asp Lys
1               5

<210> SEQ ID NO 4
<211> LENGTH: 380
<212> TYPE: PRT
<213> ORGANISM: Artificial Sequence
<220> FEATURE:
<223> OTHER INFORMATION: Description of Artificial Sequence: Skp2 deltaF

<400> SEQUENCE: 4

Met His Arg Lys His Leu Gln Glu Ile Pro Asp Gln Ser Gly Asn Val
1               5                   10                  15

Thr Thr Ser Phe Thr Trp Gly Trp Asp Ser Ser Lys Thr Ser Glu Leu
            20                  25                  30

Leu Ser Gly Met Gly Val Ser Ala Leu Glu Lys Glu Val Asp Ser
        35                  40                  45

Glu Asn Ile Pro His Gly Leu Leu Ser Asn Leu Gly His Pro Gln Ser
    50                  55                  60

Pro Pro Arg Lys Arg Val Lys Gly Lys Gly Ser Asp Lys Asp Phe Val
65                  70                  75                  80

Ile Ile Arg Arg Pro Lys Leu Ser Arg Glu Asn Phe Pro Gly Ser Leu
                85                  90                  95

Asp Leu Ala Gly Lys Asn Leu His Pro Asp Val Thr Val Arg Leu Leu
            100                 105                 110

Ser Arg Gly Val Val Ala Phe Arg Cys Pro Arg Ser Phe Met Glu Gln
        115                 120                 125

Pro Leu Gly Glu Ser Phe Ser Ser Phe Arg Val Gln His Met Asp Leu
    130                 135                 140

Ser Asn Ser Val Ile Asn Val Ser Asn Leu His Lys Ile Leu Ser Glu
145                 150                 155                 160

Cys Ser Lys Leu Gln Asn Leu Ser Leu Glu Gly Leu Gln Leu Ser Asp
                165                 170                 175

Pro Ile Val Lys Thr Leu Ala Gln Asn Glu Asn Leu Val Arg Leu Asn
            180                 185                 190
```

```
Leu Cys Gly Cys Ser Gly Phe Ser Glu Ser Ala Val Ala Thr Leu Leu
                195                 200                 205

Ser Ser Cys Ser Arg Leu Asp Glu Leu Asn Leu Ser Trp Cys Phe Asp
210                 215                 220

Phe Thr Glu Lys His Val Gln Ala Ala Val Ala His Leu Pro Asn Thr
225                 230                 235                 240

Ile Thr Gln Leu Asn Leu Ser Gly Tyr Arg Lys Asn Leu Gln Lys Thr
                245                 250                 255

Asp Leu Cys Thr Ile Ile Lys Arg Cys Pro Asn Leu Ile Arg Leu Asp
                260                 265                 270

Leu Ser Asp Ser Ile Met Leu Lys Asn Asp Cys Phe Pro Glu Phe Phe
                275                 280                 285

Gln Leu Asn Tyr Leu Gln His Leu Ser Leu Ser Arg Cys Tyr Asp Ile
        290                 295                 300

Ile Pro Asp Thr Leu Leu Glu Leu Gly Glu Ile Pro Thr Leu Lys Thr
305                 310                 315                 320

Leu Gln Val Phe Gly Ile Val Pro Glu Gly Thr Leu Gln Leu Leu Arg
                325                 330                 335

Glu Ala Leu Pro Arg Leu Gln Ile Asn Cys Ala Tyr Phe Thr Thr Ile
                340                 345                 350

Ala Arg Pro Thr Met Asp Ser Lys Lys Asn Leu Glu Ile Trp Gly Ile
                355                 360                 365

Lys Cys Arg Leu Thr Leu Gln Lys Pro Ser Cys Leu
                370                 375                 380

<210> SEQ ID NO 5
<211> LENGTH: 660
<212> TYPE: PRT
<213> ORGANISM: Artificial Sequence
<220> FEATURE:
<223> OTHER INFORMATION: Description of Artificial Sequence: Fbw7 deltaF

<400> SEQUENCE: 5

Met Asn Gln Glu Leu Leu Ser Val Gly Ser Lys Arg Arg Arg Thr Gly
1               5                   10                  15

Gly Ser Leu Arg Gly Asn Pro Ser Ser Gln Val Asp Glu Glu Gln
            20                  25                  30

Met Asn Arg Val Val Glu Glu Glu Gln Gln Gln Leu Arg Gln Gln
            35                  40                  45

Glu Glu Glu His Thr Ala Arg Asn Gly Glu Val Val Gly Val Glu Pro
    50                  55                  60

Arg Pro Gly Gly Gln Asn Asp Ser Gln Gln Gly Gln Leu Glu Glu Asn
65                  70                  75                  80

Asn Asn Arg Phe Ile Ser Val Asp Glu Asp Ser Ser Gly Asn Gln Glu
                85                  90                  95

Glu Gln Glu Glu Asp Glu Glu His Ala Gly Glu Gln Asp Glu Glu Asp
            100                 105                 110

Glu Glu Glu Glu Glu Met Asp Gln Glu Ser Asp Asp Phe Asp Gln Ser
        115                 120                 125

Asp Asp Ser Ser Arg Glu Asp Glu His Thr His Thr Asn Ser Val Thr
130                 135                 140

Asn Ser Ser Ser Ile Val Asp Leu Pro Val His Gln Leu Ser Ser Pro
                145                 150                 155                 160

Phe Tyr Thr Lys Thr Thr Lys Met Lys Arg Lys Leu Asp His Gly Ser
                165                 170                 175
```

```
Glu Val Arg Ser Phe Ser Leu Gly Lys Lys Pro Cys Lys Val Ser Glu
            180                 185                 190

Tyr Thr Ser Thr Thr Gly Leu Val Pro Cys Ser Ala Thr Pro Thr Thr
        195                 200                 205

Phe Gly Asp Leu Arg Ala Ala Asn Gly Gln Gly Gln Gln Arg Arg Arg
    210                 215                 220

Ile Thr Ser Val Gln Pro Pro Thr Gly Leu Gln Glu Trp Leu Lys Met
225                 230                 235                 240

Phe Gln Ser Trp Ser Gly Pro Glu Lys Leu Leu Ala Leu Asp Glu Leu
                245                 250                 255

Ile Asp Ser Cys Glu Pro Thr Gln Val Lys His Met Met Gln Val Ile
        260                 265                 270

Glu Pro Gln Leu Gln Cys Lys Glu Glu Gly Ile Asp Glu Pro Leu His
    275                 280                 285

Ile Lys Arg Arg Lys Val Ile Lys Pro Gly Phe Ile His Ser Pro Trp
        290                 295                 300

Lys Ser Ala Tyr Ile Arg Gln His Arg Ile Asp Thr Asn Trp Arg Arg
305                 310                 315                 320

Gly Glu Leu Lys Ser Pro Lys Val Leu Lys Gly His Asp Asp His Val
                325                 330                 335

Ile Thr Cys Leu Gln Phe Cys Gly Asn Arg Ile Val Ser Gly Ser Asp
        340                 345                 350

Asp Asn Thr Leu Lys Val Trp Ser Ala Val Thr Gly Lys Cys Leu Arg
    355                 360                 365

Thr Leu Val Gly His Thr Gly Gly Val Trp Ser Ser Gln Met Arg Asp
370                 375                 380

Asn Ile Ile Ile Ser Gly Ser Thr Asp Arg Thr Leu Lys Val Trp Asn
385                 390                 395                 400

Ala Glu Thr Gly Glu Cys Ile His Thr Leu Tyr Gly His Thr Ser Thr
                405                 410                 415

Val Arg Cys Met His Leu His Glu Lys Arg Val Val Ser Gly Ser Arg
        420                 425                 430

Asp Ala Thr Leu Arg Val Trp Asp Ile Glu Thr Gly Gln Cys Leu His
    435                 440                 445

Val Leu Met Gly His Val Ala Ala Val Arg Cys Val Gln Tyr Asp Gly
450                 455                 460

Arg Arg Val Val Ser Gly Ala Tyr Asp Phe Met Val Lys Val Trp Asp
465                 470                 475                 480

Pro Glu Thr Glu Thr Cys Leu His Thr Leu Gln Gly His Thr Asn Arg
                485                 490                 495

Val Tyr Ser Leu Gln Phe Asp Gly Ile His Val Val Ser Gly Ser Leu
        500                 505                 510

Asp Thr Ser Ile Arg Val Trp Asp Val Glu Thr Gly Asn Cys Ile His
    515                 520                 525

Thr Leu Thr Gly His Gln Ser Leu Thr Ser Gly Met Glu Leu Lys Asp
530                 535                 540

Asn Ile Leu Val Ser Gly Asn Ala Asp Ser Thr Val Lys Ile Trp Asp
545                 550                 555                 560

Ile Lys Thr Gly Gln Cys Leu Gln Thr Leu Gln Gly Pro Asn Lys His
                565                 570                 575

Gln Ser Ala Val Thr Cys Leu Gln Phe Asn Lys Asn Phe Val Ile Thr
        580                 585                 590

Ser Ser Asp Asp Gly Thr Val Lys Leu Trp Asp Leu Lys Thr Gly Glu
```

```
            595                 600                 605
Phe Ile Arg Asn Leu Val Thr Leu Glu Ser Gly Gly Ser Gly Gly Val
            610                 615                 620
Val Trp Arg Ile Arg Ala Ser Asn Thr Lys Leu Val Cys Ala Val Gly
625                 630                 635                 640
Ser Arg Asn Gly Thr Glu Glu Thr Lys Leu Leu Val Leu Asp Phe Asp
                    645                 650                 655
Val Asp Met Lys
            660

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: peptide
      with ubiquitylation
<220> FEATURE:
<221> NAME/KEY: MOD_RES
<222> LOCATION: (5)..(5)
<223> OTHER INFORMATION: Lysine residues modified by diglycine
<220> FEATURE:
<221> NAME/KEY: MOD_RES
<222> LOCATION: (8)..(8)
<223> OTHER INFORMATION: Cysteine residues modified methylthiolation

<400> SEQUENCE: 6

Ile Ala Pro Pro Xaa Leu Ala Xaa Arg
1               5

<210> SEQ ID NO 7
<211> LENGTH: 14
<212> TYPE: PRT
<213> ORGANISM: Artificial Sequence
<220> FEATURE:
<223> OTHER INFORMATION: Description of Artificial Sequence: peptide
      with ubiquitylation site
<220> FEATURE:
<221> NAME/KEY: MOD_RES
<222> LOCATION: (1)..(1)
<223> OTHER INFORMATION: Lysine residues modified by diglycine
<220> FEATURE:
<221> NAME/KEY: MOD_RES
<222> LOCATION: (13)..(13)
<223> OTHER INFORMATION: Lysine residues modified by diglycine

<400> SEQUENCE: 7

Xaa Arg Pro Ala Thr Asp Asp Ser Ser Thr Gln Asn Xaa Arg
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: peptide
      with ubiquitylation site
<220> FEATURE:
<221> NAME/KEY: MOD_RES
<222> LOCATION: (4)..(4)
<223> OTHER INFORMATION: Methionine residues modified by oxidation
<220> FEATURE:
<221> NAME/KEY: MOD_RES
<222> LOCATION: (11)..(11)
<223> OTHER INFORMATION: Lysine residues modified by diglycine

<400> SEQUENCE: 8

Gln Thr Ser Xaa Thr Asp Phe Tyr His Ser Xaa Arg
1               5                   10
```

<210> SEQ ID NO 9
<211> LENGTH: 577
<212> TYPE: PRT
<213> ORGANISM: Artificial Sequence
<220> FEATURE:
<223> OTHER INFORMATION: Description of Artificial Sequence: Fbxo21 deltaF

<400> SEQUENCE: 9

```
Met Ala Ala Ala Val Asp Ser Ala Met Glu Val Val Pro Ala Leu
1               5                   10                  15

Ala Glu Glu Ala Ala Pro Glu Val Ala Gly Leu Ala Arg Trp Pro Ser
            20                  25                  30

Leu Met Lys His Tyr Ser Pro Thr Asp Tyr Val Asn Trp Leu Glu Glu
        35                  40                  45

Tyr Lys Val Arg Gln Lys Ala Gly Leu Glu Ala Arg Lys Ile Val Ala
    50                  55                  60

Ser Phe Ser Lys Arg Phe Phe Ser Glu His Val Pro Cys Asn Gly Phe
65                  70                  75                  80

Ser Asp Ile Glu Asn Leu Glu Gly Pro Glu Ile Phe Phe Glu Asp Glu
                85                  90                  95

Leu Val Cys Ile Leu Asn Met Glu Gly Arg Lys Ala Leu Thr Trp Lys
            100                 105                 110

Tyr Tyr Ala Lys Lys Ile Leu Tyr Leu Arg Gln Gln Lys Ile Leu
        115                 120                 125

Asn Asn Leu Lys Ala Phe Leu Gln Gln Pro Asp Asp Tyr Glu Ser Tyr
130                 135                 140

Leu Glu Gly Ala Val Tyr Ile Asp Gln Tyr Cys Asn Pro Leu Ser Asp
145                 150                 155                 160

Ile Ser Leu Lys Asp Ile Gln Ala Gln Ile Asp Ser Ile Val Glu Leu
                165                 170                 175

Val Cys Lys Thr Leu Arg Gly Ile Asn Ser Arg His Pro Ser Leu Ala
            180                 185                 190

Phe Lys Ala Gly Glu Ser Ser Met Ile Met Glu Ile Glu Leu Gln Ser
        195                 200                 205

Gln Val Leu Asp Ala Met Asn Tyr Val Leu Tyr Asp Gln Leu Lys Phe
    210                 215                 220

Lys Gly Asn Arg Met Asp Tyr Tyr Asn Ala Leu Asn Leu Tyr Met His
225                 230                 235                 240

Gln Val Leu Ile Arg Arg Thr Gly Ile Pro Ile Ser Met Ser Leu Leu
                245                 250                 255

Tyr Leu Thr Ile Ala Arg Gln Leu Gly Val Pro Leu Glu Pro Val Asn
            260                 265                 270

Phe Pro Ser His Phe Leu Leu Arg Trp Cys Gln Gly Ala Glu Gly Ala
        275                 280                 285

Thr Leu Asp Ile Phe Asp Tyr Ile Tyr Ile Asp Ala Phe Gly Lys Gly
    290                 295                 300

Lys Gln Leu Thr Val Lys Glu Cys Glu Tyr Leu Ile Gly Gln His Val
305                 310                 315                 320

Thr Ala Ala Leu Tyr Gly Val Val Asn Val Lys Lys Val Leu Gln Arg
                325                 330                 335

Met Val Gly Asn Leu Leu Ser Leu Gly Lys Arg Glu Gly Ile Asp Gln
            340                 345                 350

Ser Tyr Gln Leu Leu Arg Asp Ser Leu Asp Leu Tyr Leu Ala Met Tyr
```

```
                355                 360                 365
Pro Asp Gln Val Gln Leu Leu Leu Gln Ala Arg Leu Tyr Phe His
370                 375                 380

Leu Gly Ile Trp Pro Glu Lys Ser Phe Cys Leu Val Leu Lys Val Leu
385                 390                 395                 400

Asp Ile Leu Gln His Ile Gln Thr Leu Asp Pro Gly Gln His Gly Ala
                405                 410                 415

Val Gly Tyr Leu Val Gln His Thr Leu Glu His Ile Glu Arg Lys Lys
            420                 425                 430

Glu Glu Val Gly Val Glu Val Lys Leu Arg Ser Asp Glu Lys His Arg
        435                 440                 445

Asp Val Cys Tyr Ser Ile Gly Leu Ile Met Lys His Lys Arg Tyr Gly
    450                 455                 460

Tyr Asn Cys Val Ile Tyr Gly Trp Asp Pro Thr Cys Met Met Gly His
465                 470                 475                 480

Glu Trp Ile Arg Asn Met Asn Val His Ser Leu Pro His Gly His His
                485                 490                 495

Gln Pro Phe Tyr Asn Val Leu Val Glu Asp Gly Ser Cys Arg Tyr Ala
            500                 505                 510

Ala Gln Glu Asn Leu Glu Tyr Asn Val Glu Pro Gln Glu Ile Ser His
        515                 520                 525

Pro Asp Val Gly Arg Tyr Phe Ser Glu Phe Thr Gly Thr His Tyr Ile
    530                 535                 540

Pro Asn Ala Glu Leu Glu Ile Arg Tyr Pro Glu Asp Leu Glu Phe Val
545                 550                 555                 560

Tyr Glu Thr Val Gln Asn Ile Tyr Ser Ala Lys Lys Glu Asn Ile Asp
                565                 570                 575

Glu

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence: peptide
      with ubiquitylation site
<220> FEATURE:
<221> NAME/KEY: MOD_RES
<222> LOCATION: (5)..(5)
<223> OTHER INFORMATION: Lysine residues modified by diglycine

<400> SEQUENCE: 10

Ile Leu Asn Glu Xaa Val Asn Thr Pro Thr Thr Thr Val Tyr Arg
1               5                   10                  15

<210> SEQ ID NO 11
<211> LENGTH: 602
<212> TYPE: PRT
<213> ORGANISM: Artificial Sequence
<220> FEATURE:
<223> OTHER INFORMATION: Description of Artificial Sequence: Fbw1 deltaF

<400> SEQUENCE: 11

Met Asp Pro Ala Glu Ala Val Leu Gln Glu Lys Ala Leu Lys Phe Met
1               5                   10                  15

Cys Ser Ser Met Pro Arg Ser Ser Leu Trp Leu Gly Cys Ser Ser Ser
            20                  25                  30

Ser Leu Ala Asp Ser Ser Met Pro Ser Ser Leu Arg Cys Leu Tyr Asn
        35                  40                  45
```

-continued

Pro Gly Thr Gly Ala Leu Thr Ala Phe Gln Asn Ser Ser Ser Glu
50                  55                  60

Arg Glu Asp Cys Asn Asn Gly Glu Pro Pro Arg Lys Ile Ile Pro Glu
65                  70                  75                  80

Lys Asn Ser Ser Leu Leu Arg Gln Thr Tyr Asn Ser Ser Cys Ala Arg
                85                  90                  95

Leu Leu Cys Leu Asn Gln Glu Thr Val Cys Leu Ala Ser Ser Thr Ala
            100                 105                 110

Met Lys Thr Glu Asn Cys Val Ala Lys Thr Lys Leu Ala Asn Gly Thr
        115                 120                 125

Ser Ser Ser Ser Met Ile Val Pro Lys Gln Arg Lys Leu Ser Ser Ala
130                 135                 140

Ser Ser Tyr Glu Lys Glu Lys Glu Leu Cys Val Lys Tyr Phe Glu Gln
145                 150                 155                 160

Trp Ser Ser Glu Ser Ser Asp Gln Val Glu Phe Val Glu His Leu Ile
                165                 170                 175

Ser Ser Gln Met Cys His Tyr Gln His Gly His Ile Asn Ser Ser Tyr
            180                 185                 190

Leu Lys Pro Pro Met Leu Gln Arg Asp Phe Ile Thr Ala Ala Leu Pro
        195                 200                 205

Pro Ala Ala Arg Gly Ser Ser Ile Glu Arg Met Val Arg Thr Asp Ser
210                 215                 220

Leu Trp Arg Gly Leu Ala Ala Glu Arg Arg Gly Trp Gly Gln Tyr Leu
225                 230                 235                 240

Phe Lys Asn Lys Pro Pro Asp Gly Asn Ala Pro Pro Asn Ser Phe
                245                 250                 255

Tyr Arg Ala Leu Tyr Pro Lys Ile Ile Gln Asp Ile Glu Thr Ile Glu
            260                 265                 270

Ser Asn Trp Arg Cys Gly Arg His Ser Leu Gln Arg Ile His Cys Arg
        275                 280                 285

Ser Glu Thr Ser Lys Gly Val Val Tyr Cys Leu Gln Tyr Asp Asp Gln
290                 295                 300

Lys Ile Val Ser Gly Leu Arg Asp Asn Thr Ile Lys Ile Trp Asp Lys
305                 310                 315                 320

Asn Thr Leu Glu Cys Lys Arg Ile Leu Thr Gly His His Thr Gly Ser
                325                 330                 335

Val Leu Cys Leu Gln Tyr Asp Glu Arg Val Ile Ile Thr Gly Ser Ser
            340                 345                 350

Asp Ser Thr Val Arg Val Trp Asp Val Asn Thr Gly Glu Met Leu Asn
        355                 360                 365

Thr Leu Ile His His His His Cys Glu Ala Val Leu His His Leu Arg
370                 375                 380

Phe Asn Asn Gly Met Met Val Thr Cys Ser Lys Asp Arg Ser Ile Ala
385                 390                 395                 400

Val Trp Asp Met Ala Ser Pro Thr Asp Ile Thr Leu Arg Arg Val Leu
                405                 410                 415

Val Gly His Arg Ala Ala Val Asn Val Val Asp Phe Asp Asp Lys Tyr
            420                 425                 430

Ile Val Ser Ala Ser Gly Asp Arg Thr Thr Ile Lys Val Trp Asn Thr
        435                 440                 445

Thr Ser Thr Thr Cys Glu Phe Val Arg Thr Leu Asn Gly His Lys Arg
450                 455                 460

Gly Ile Ala Cys Leu Gln Tyr Arg Asp Arg Leu Val Val Ser Gly Ser
465                 470                 475                 480

Ser Asp Asn Thr Ile Arg Leu Trp Asp Ile Glu Cys Gly Ala Cys Leu
            485                 490                 495

Arg Val Leu Glu Gly His Glu Glu Leu Val Arg Cys Ile Arg Phe Asp
        500                 505                 510

Asn Lys Arg Ile Val Ser Gly Ala Tyr Asp Gly Lys Ile Lys Val Trp
    515                 520                 525

Asp Leu Val Ala Ala Leu Asp Pro Arg Ala Pro Ala Gly Thr Leu Cys
530                 535                 540

Leu Arg Thr Leu Val Glu His Ser Gly Arg Val Phe Arg Leu Gln Phe
545                 550                 555                 560

Asp Glu Phe Gln Ile Val Ser Ser Ser His Asp Asp Thr Ile Leu Ile
            565                 570                 575

Trp Asp Phe Leu Asn Asp Pro Ala Ala Gln Ala Glu Pro Pro Arg Ser
        580                 585                 590

Pro Ser Arg Thr Tyr Thr Tyr Ile Ser Arg
    595                 600

<210> SEQ ID NO 12
<211> LENGTH: 17
<212> TYPE: PRT
<213> ORGANISM: Artificial Sequence
<220> FEATURE:
<223> OTHER INFORMATION: Description of Artificial Sequence: peptide
      with ubiquitylation site
<220> FEATURE:
<221> NAME/KEY: MOD_RES
<222> LOCATION: (9)..(9)
<223> OTHER INFORMATION: Lysine residues modified by diglycine

<400> SEQUENCE: 12

Asn Ser Ser Thr Tyr Trp Glu Gly Xaa Ala Asp Met Glu Thr Leu Gln
1               5                   10                  15

Arg

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: peptide
      with ubiquitylation site
<220> FEATURE:
<221> NAME/KEY: MOD_RES
<222> LOCATION: (6)..(6)
<223> OTHER INFORMATION: Lysine residues modified by diglycine

<400> SEQUENCE: 13

Phe Gln Glu Glu Ala Xaa Asn Arg
1               5

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: peptide
      with ubiquitylation site
<220> FEATURE:
<221> NAME/KEY: MOD_RES
<222> LOCATION: (4)..(4)
<223> OTHER INFORMATION: Lysine residues modified by diglycine

<400> SEQUENCE: 14

```
His Thr Gly Xaa Ile Lys
1               5

<210> SEQ ID NO 15
<211> LENGTH: 14
<212> TYPE: PRT
<213> ORGANISM: Artificial Sequence
<220> FEATURE:
<223> OTHER INFORMATION: Description of Artificial Sequence: peptide
      with ubiquitylation site
<220> FEATURE:
<221> NAME/KEY: MOD_RES
<222> LOCATION: (10)..(10)
<223> OTHER INFORMATION: Lysine residues modified by diglycine
<220> FEATURE:
<221> NAME/KEY: MOD_RES
<222> LOCATION: (11)..(11)
<223> OTHER INFORMATION: Methionine residues modified by oxidation

<400> SEQUENCE: 15

Val Ser Ala Ala Leu Glu Glu Ala Asp Xaa Xaa Phe Leu Arg
1               5                   10

<210> SEQ ID NO 16
<211> LENGTH: 27
<212> TYPE: PRT
<213> ORGANISM: Artificial Sequence
<220> FEATURE:
<223> OTHER INFORMATION: Description of Artificial Sequence: peptide
      with ubiquitylation site
<220> FEATURE:
<221> NAME/KEY: MOD_RES
<222> LOCATION: (12)..(12)
<223> OTHER INFORMATION: Methionine residues modified by oxidation
<220> FEATURE:
<221> NAME/KEY: MOD_RES
<222> LOCATION: (20)..(20)
<223> OTHER INFORMATION: Methionine residues modified by oxidation
<220> FEATURE:
<221> NAME/KEY: MOD_RES
<222> LOCATION: (26)..(26)
<223> OTHER INFORMATION: Lysine residues modified by diglycine

<400> SEQUENCE: 16

Ser Gly Ala Gln Gln Leu Glu Glu Glu Gly Pro Xaa Glu Glu Glu
1               5                   10                  15

Ala Gln Pro Xaa Ala Ala Pro Glu Gly Xaa Arg
            20                  25
```